(12) United States Patent
Statnikov et al.

(10) Patent No.: US 7,912,698 B2
(45) Date of Patent: Mar. 22, 2011

(54) METHOD AND SYSTEM FOR AUTOMATED SUPERVISED DATA ANALYSIS

(76) Inventors: Alexander Statnikov, Nashville, TN (US); Constantin F. Aliferis, Nashville, TN (US); Ioannis Tsamardinos, Nashville, TN (US); Nafeh Fananapazir, Nashville, TN (US)

( * ) Notice: Subject to any disclaimer, the term of this patent is extended or adjusted under 35 U.S.C. 154(b) by 1037 days.

(21) Appl. No.: 11/510,847

(22) Filed: Aug. 28, 2006

(65) Prior Publication Data
US 2007/0122347 A1  May 31, 2007

Related U.S. Application Data

(60) Provisional application No. 60/711,402, filed on Aug. 26, 2005.

(51) Int. Cl.
*G06F 17/20* (2006.01)
(52) U.S. Cl. ................... 704/8; 704/9; 704/257
(58) Field of Classification Search .............. 704/9, 245, 704/250, 255, 257, 270; 702/19; 250/458.1, 250/258.1
See application file for complete search history.

(56) References Cited

U.S. PATENT DOCUMENTS

| | | | | |
|---|---|---|---|---|
| 7,309,867 B2 * | 12/2007 | Costa et al. | ............. | 250/458.1 |
| 2003/0195706 A1 * | 10/2003 | Korenberg | ............. | 702/19 |

OTHER PUBLICATIONS

Aliferis, C.F. et al, *HITON: A Novel Blanket Algorithm for Optimal Variable Selection*, AMIA Symposium (2003).
Balmain, A., Gray, J. & Ponder, B., *The Genetics and Genomics of Cancer*, Nat. Genet., 33 Suppl.:238-44 (Mar. 2003).
Dudoit, A. &. van der Laan, M.J., *Asymptotics of Cross-Validated Risk Estimation in Model Selection and Performance Assessment*, U.C. Berkeley Division of Biostatistics Working Paper Series, Working Paper 126 (Feb. 5, 2003).
Golub, T.R. et al., *Molecular Classification of Cancer: Class Discovery and Class Prediction by Gene Expression Monitoring*, Science, 286(5439):531-7 (Oct. 15, 1999).
Ntzani, E.E. & Ioannidis, J.P., *Predictive Ability of DNA Microarrays for Cancer Outcomes and Correlates: An Emperical Assessment*, Lancet, 362(9394):1439-44 (Nov. 1, 2003).
Ritthoff, O. et al., *Yale: Yet Another Machine Learning Environment*, LLWA 01-Tagungsband der GI-Workshop-Woche Lernen—Lehren—Wissen—Adaptivitat, No. Nr. 763, pp. 84-92, Dortmund, Germany (2001).
Scheffer, T., Ph.D thesis, *Error Estimation and Model Selection*, Technischen Universitat Berlin, School of Computer Science (1999).
Tsmardinos, I. et al., *Time and Sample Efficient Discovery of Markov Blankets and Direct Casual Relations*, Department of Biomedical Informatics, published in 2002.

* cited by examiner

*Primary Examiner* — Huyen X. Vo
(74) *Attorney, Agent, or Firm* — Miles & Stockbridge P.C.

(57) ABSTRACT

The invention relates to a method for automatically analyzing data and constructing data classification models based on the data. In an embodiment of the method, the method includes selecting a best combination of methods from a plurality of classification, predictor selection, and data preparatory methods; and determining a best model that corresponds to one or more best parameters of the classification, predictor selection, and data preparatory methods for the data to be analyzed. The best model; and returning a small set of predictors sufficient for the classification task.

18 Claims, 14 Drawing Sheets

METHOD AND SYSTEM FOR AUTOMATED SUPERVISED DATA ANALYSIS

CROSS-REFERENCE TO RELATED APPLICATION

This application claims benefit of priority to U.S. Provisional Application No. 60/711,402, filed on Aug. 26, 2005, which is hereby incorporated by reference herein in its entirety.

REFERENCE TO GOVERNMENT GRANT

This invention was made in part with Government support under Grant Nos. ROI LM007948-01 and P20 LM 007613-01, awarded by the National Institute of Health/National Library of Medicine; and Grant No. T15 LM07450-01 (NF), also awarded by the National Institute of Health/National Library of Medicine. The Government has certain rights in this invention.

FIELD OF THE INVENTION

The invention relates to providing automated supervised data analysis. More specifically, the invention relates to a automatically constructing optimal models, estimating performance of these models in future applications to a new population of subjects in a statistically unbiased fashion, and selecting a reduced set of predictor variables required for target variable prediction while preserving or even improving classification performance.

BACKGROUND

Development of diagnostic and outcome prediction models and discovery from DNA microarray data is of great interest in bioinformatics and medicine. Diagnostic models from gene expression data go beyond traditional histopathology and can provide accurate, resource-efficient, and replicable diagnosis. (See, Golub T R, Slonim D K, Tamayo P, Huard C, Gaasenbeek M, Mesirov J P, Coller H, Loh M L, Downing J R, Caligiuri M A, Bloomfield C D, Lander E S, "Molecular classification of cancer: class discovery and class prediction by gene expression monitoring." Science, 1999 Oct. 15; 286(5439):531-7.) Furthermore, biomarker discovery in high-dimensional microarray data facilitates discoveries about the biology. (See, Balmain A, Gray J, Ponder B, "The genetics and genomics of cancer." Nat. Genet. 2003 March; 33 Suppl:238-44. Review.)

Building classification models from microarray gene expression data has three challenging components: collection of samples, assaying, and statistical analysis. A typical statistical analysis process takes from a few weeks to several months and involves interactions of many specialists: clinical researchers, statisticians, bioinformaticians, and programmers. As a result, statistical analysis is a serious bottleneck in the development of molecular microarray-based diagnostic, prognostic or individualized treatment models (typically referred to also as "personalized medicine").

Even if the long duration and high expenses of the statistical analyses process as described above is considered acceptable, its results frequently suffer from two major pitfalls. First, as documented in many published studies, analyses are affected by the problem of overfitting; that is creating predictive models that may not generalize well to new data from the same disease types and data distribution despite excellent performance on the training set. Since many algorithms are highly parametric and datasets consist of a relatively small number of high-dimensional samples, it is easy to overfit both the classifiers and the gene selection procedures especially when using intensive model search and powerful learners. In a recent meta-analytic assessment of 84 published microarray cancer outcome predictive studies (see, Ntzani E E, Ioannidis J P. "Predictive ability of DNA microarrays for cancer outcomes and correlates: an empirical assessment." Lancet. 2003 Nov 1, 362(9394): 1439-44.), it was found that only 26% of studies in this domain attempted independent validation or cross-validation of their findings. Thus it is doubtful whether these models will generalize well to unseen patients. The second methodological problem is underfitting, which results in classifiers that are not optimally performing due to limited search in the space of classification models. In particular, this is manifested by application of a specific learning algorithm without consideration of alternatives, or use of parametric learners with unoptimized default values of parameters (i.e., without systematically searching for the best parameters).

Sixteen software systems currently available for supervised analysis of microarray data are identified in Appendix A. However, all of the identified systems have several of the following limitations. First, neither system automatically optimizes the parameters and the choice of both classification and gene selection algorithms (also known as model selection) while simultaneously avoiding overfitting. The user of these systems is left with two choices: either to avoid rigorous model selection and possibly discover a suboptimal model, or to experiment with many different parameters and algorithms and select the model with the highest cross-validation performance. The latter is subject to overfitting primarily due to multiple-testing, since parameters and algorithms are selected after all the testing sets in cross-validation have been seen by the algorithms. (See, Statnikov A, Aliferis C F, Tsamardinos I, Hardin D, Levy S, "A comprehensive evaluation of multicategory classification methods for microarray gene expression cancer diagnosis." Bioinformatics, 2005 Mar. 1; 21(5):631-43.) Second, a typical software system either offers an overabundance of algorithms or algorithms with unknown performance. Thus is it not clear to the user how to choose an optimal algorithm for a given data analysis task. Third, the software systems address needs of experienced analysts. However, there is a need to use these systems (and still achieve good results) by users who know little about data analysis (e.g., biologists and clinicians).

There is also a generic machine learning environment YALE that allows specification and execution of different chains of steps for data analysis, especially feature selection and model selection, and multistrategy learning. (See, Ritthoff O, et al., "Yale: Yet Another Machine Learning Environment", LLWA 01—Tagungsband der GI-Workshop-Woche Lernen—Lehren—Wissen—Adaptivität, No. Nr. 763, pages 84-92, Dortmund, Germany, 2001.) In particular, this environment allows selection of models by cross-validation and estimation of performance by nested cross-validation. However, the principal difference of YALE with the invention is that YALE is not a specific method but rather a high-level programming language that potentially allows implementation of the invention in the same generic sense that a general-purpose programming language can be used to implement any computable functionality. The existing version of YALE 3.0 is not packaged with the ready-to-use implementation of the invention.

All the above problems are solved by the subsequently described various embodiments of the present invention.

BRIEF DESCRIPTION OF THE DRAWINGS

The present invention will be described with reference to the accompanying drawings.

DETAILED DESCRIPTION

Embodiments of the present invention comprise a data analysis method, which may be reduced to practice by means of a computer program. In accordance with one or more embodiments of the present invention, the computer program may perform a supervised analysis of data (e.g., microarray gene expression data). In particular, the program may accept as input a set of data measurements for a set of subjects and a target (response) variable (e.g., in biomedical applications the diagnosis, clinical outcome or other clinically interesting information) about each one of the subjects. The program may then interact with a human user or operate in a fully automatic mode to:

(1) construct optimal models capable of prediction of the target variable for a subject given the instantiated vector of its predictor variables;
(2) estimate performance of these models in future applications to a new population of subjects (different than the training data) in a statistically unbiased fashion;
(3) select a reduced set of predictor variables required for target variable prediction while preserving or even improving classification performance.

In general, in accordance with the embodiments of the present invention, a model may be defined as the specific choice of algorithms (for example, for normalization/data preparation, classification, predictor selection) and the parameters associated with each algorithm. Embodiments of the present invention may be designed to: 1) estimate performance of a given model by cross-validation; 2) choose an optimal model from among multiple possible models by cross-validation; 3) simultaneously perform tasks 1 and 2; and 4) apply an obtained model, for example, from tasks 2 or 3, to new data.

Figure 1:
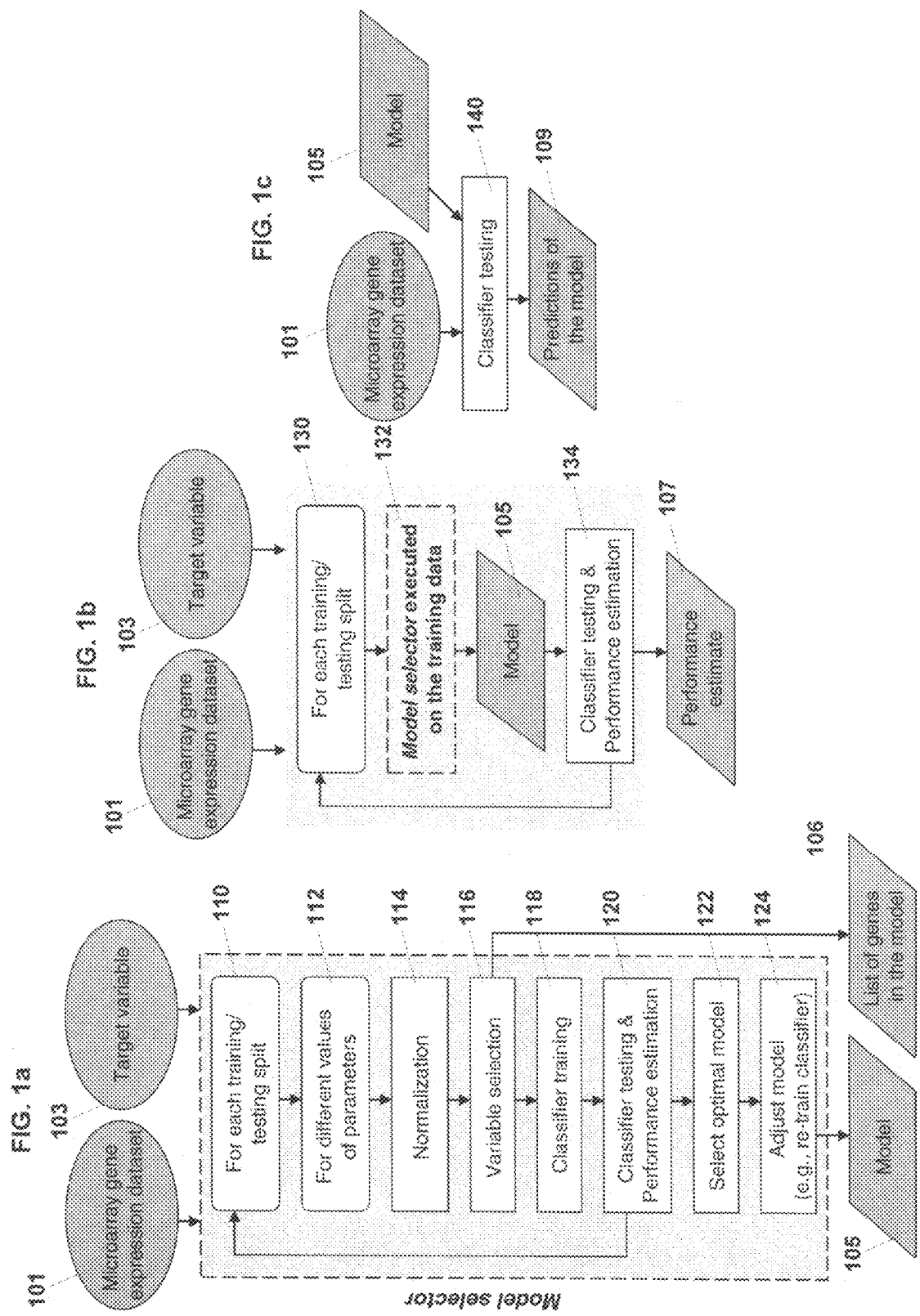
FIG. 1a is a flow diagram of a method for selecting a data classification model and reduced set of variables based on data split into multiple training data subsets and separate test subsets, in accordance with one or more embodiments of the present invention.
FIG. 1b is a flow diagram of a method for estimating performance in a selected data classification model using data split into multiple training data subsets and separate test subsets, in accordance with one or more embodiments of the present invention.
FIG. 1c is a flow diagram of a method for applying a data classification model to new data, in accordance with one or more embodiments of the present invention.

FIGS. 1a-1c show the high-level functionality of the invention to include: (a) model selection (e.g., variable/gene selection), (b) performance estimation, and (c) application of the existing model to new data. Specifically, FIG. 1a is a flow diagram of a method for selecting a data classification model based on data split into multiple training data subsets and separate test subsets, in accordance with one or more embodiments of the present invention. In FIG. 1a, a microarray gene expression dataset 101 and a target variable 103 may be used by the method to produce a model 105 and a list of variables in the model 106. The method may iteratively perform for each training/testing dataset split 110 and for different values of parameters 112, normalization 114 of the data. The method may further perform variable selection 116 to select the optimal variables for the normalized data and output the list of genes in the model 106 determined as a result of the variable selection 116. The method may still further perform classifier training 118 using the different values of parameters and selected variables. The method may yet further perform classifier testing and performance estimation 120 on each of the previously trained classifiers using the testing dataset that was not used in the training. If additional classifier training is necessary, the method loops back and continues with the next training/testing dataset split 110. If no additional classifier training is necessary, the method may select the optimal model 122 from the trained classifiers, re-train the selected classifier 124, and output the optimal model 105.

FIG. 1*b* is a flow diagram of a method for estimating performance in a selected data classification model using data split into multiple training data subsets and separate test subsets, in accordance with one or more embodiments of the present invention. In FIG. 1*b*, microarray gene expression dataset 101 and target variable 103 may be used by the method to produce a performance estimate 107 for model 105. The method may, for each training/testing dataset split 130, iteratively execute a model selector 132, such as shown in FIG. 1*a*, on the training dataset to select the optimal model 105 and perform classifier testing and performance estimation 134 of the model 105. If additional training/testing datasets are available, the method loops back and continues with the next training/testing dataset split 130. If no additional training/testing datasets are available, the method may output an optimal performance estimate 107 for model 105.

FIG. 1*c* is a flow diagram of a method for applying a data classification model to new data, in accordance with one or more embodiments of the present invention. In FIG. 1*c*, microarray gene expression dataset 101 and model 105 may be used by the method to produce predictions 109 of how model 105 would perform using new data. In the method the model 105 would be evaluated by testing the classifier 140 in model 105 on new data to produce the predictions 109.

A biomedicine-based embodiment of the present invention, may be implemented as a software program that may function as a "diagnostic decision support system" where a healthcare professional constructs models and/or uses previously saved models to assist clinical decision-making. An additional biomedical context may include that of biomedical research seeking to unravel gene-gene functional relationships and gene-disease predictive and causal (functional) relationships. Details of a specific embodiment of the software program may be found in Statnikov A, Tsamardinos I, Dosbayev Y, Aliferis C F, "GEMS: A System for Automated Cancer Diagnosis and Biomarker Discovery from Microarray Gene Expression Data," Int J Med Inform., 2005 August; 74(7-8): 493-501; Statnikov A, Aliferis C F, Tsamardinos I, Hardin D, Levy S, "A comprehensive evaluation of multicategory classification methods for microarray gene expression cancer diagnosis," Bioinformatics, 2005 Mar. 1; 21(5):631-43; and Statnikov A, Aliferis C F, Tsamardinos I, "Methods for Multi-category Cancer Diagnosis from Gene Expression Data: A Comprehensive Evaluation to Inform Decision Support System Development," Medinfo, 2004, each of which are hereby incorporated by reference herein in their entireties.

Additional embodiments of the method may address analysis of a plurality of other data types as described in the subsequent paragraphs.

Figure 2:
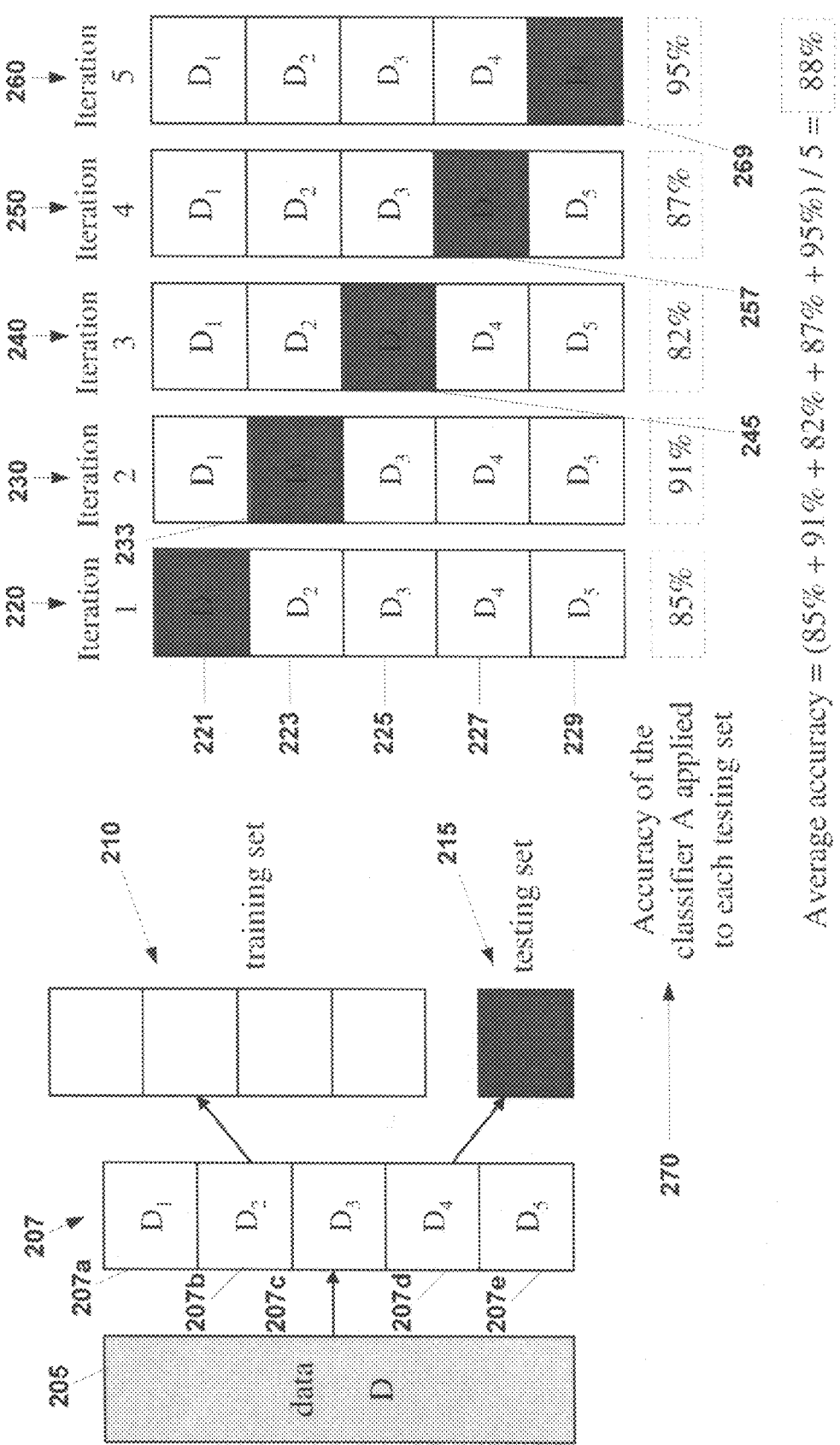
FIG. 2 is a block diagram of how a data set may be split into training sets/subsets and a testing set/subset for a 5-fold cross-validation for performance estimation of a classification model using the data set/subsets and a single model parameter, in accordance with one or more embodiments of the present invention.

Optimal Model Selection. The process of optimal model construction may be based on n-fold cross-validation, a method for providing an estimate of the performance of a specific parameterization of a classification model produced by a learning procedure A on available data D. FIG. 2 is a block diagram of how a data set 205 may be split into N equal, non-overlapping subsets 207, which are then grouped into a training set 210 and a testing set 215. Each subset may be referred to as $D_i$, where i=1 to N. For example, for a 5-fold cross-validation (i.e., N=5) performance estimation of a classification model using data D, as seen in FIG. 2, five (5) equal, non-overlapping subsets $D_1$ 207a, $D_2$ 207b, $D_3$ 207c, $D_4$ 207d, and $D_5$ 207e may be created for use with a single model parameter, in accordance with one or more embodiments of the present invention. In some embodiments of the present invention, no model parameters may also be used.

The measure of performance is accuracy of the classification. For example, in the 5-fold cross-validation in FIG. 2, data D is partitioned into 5 non-overlapping subsets of cases ($D_1$ 207a, $D_2$ 207b, $D_3$ 207c, $D_4$ 207d, and $D_5$ 207e) while preserving a portion of cases from different diagnostic/outcome category in each subset. For example, in FIG. 2, for the 5 non-overlapping subsets, there are 5 different possible combinations of 4 training data sets and 1 testing set (shown as the shaded data set), which may be referred to as splits and/or iterations are labeled Iteration 1, Iteration 2, Iteration 3, Iteration 4, and Iteration 5, respectively, 220, 230, 240, 250, 260. As seen in Iteration 1 220, a first data subset $D_1$ 221 is used as the testing set and a second $D_2$ 222, a third $D_3$ 223, a fourth $D_4$ 227 and a fifth $D_5$ 229 data subsets are used as the training set 210. Each subsequent iteration uses a different subset (e.g., Iteration 2 230 uses $D_2$, Iteration 3 240 uses $D_3$, Iteration 4 uses $D_4$ and Iteration 5 uses $D_5$) as the testing set and the remaining data subsets as the training sets. In this example the data sets are all balanced, because each has a total of 5 subsets, with 4 subsets being used for training and 1 subset being used for testing. Using the method shown in FIG. 1, the following is repeated 5 times: A is trained on the 4 subsets (training set) and tested on the holdout subset (testing set). Finally, the average performance over the 5 testing sets 270 is reported. This procedure is referred to as cross-validation for parameter optimization. As seen in FIG. 2, the accuracy of classifier A for the 5 iterations range from 82% to 95% accuracy, which results in a 5-fold cross-validation accuracy of classifier A as it is applied to data D of (85%+91%+82%+87%+95%)/5=88%.

In general, for a dataset partitioned into N subsets there will N different splits with each split having a training set of N−1 subsets and a testing set of 1 subset, where the testing set is different in each of the splits. Therefore, for the example in FIG. 2, since there are N=5 subsets, each training set is N−1=5−1=4 subsets, and each testing set is 1 subset. For example, in iteration 1 subset $D_1$ 221 is the testing set, in iteration 2 subset $D_2$ 243 is the testing set, in iteration 3 subset $D_3$ 245 is the testing set, in iteration 4 subset $D_4$ 257 is the testing set, and in iteration 5 $D_5$ 269 subset is the testing set. Although the order is sequential in the example, it is not necessary that the splits be organized as such.

When a classifier that is used for learning is parametric, the optimal values of its parameters may be estimated to produce a final model. Assuming that the classifier can be applied with a vector of parameter values and there are m possible instantiations of this vector: $\{\alpha_1, \alpha_2, \alpha_3, \ldots, \alpha_{m-1}, \alpha_m\}$. Here $\alpha_i$ may contain, but is not limited to, the following values:

- Choice of classification algorithms (e.g., K-Nearest Neighbors, Support Vector Machines);
- Parameters of the specific classification algorithms (e.g., number of neighbors K for K-Nearest Neighbors, penalty parameter C for Support Vector Machines);
- Choice of algorithms applied prior to classification, such as variable selection, normalization, imputation, and others (e.g., univariate variable selection by ANOVA, multivariate variable selection by RFE);
- Parameters of algorithms applied prior to classification (e.g., number of variables to be used for classification).

Figure 3:
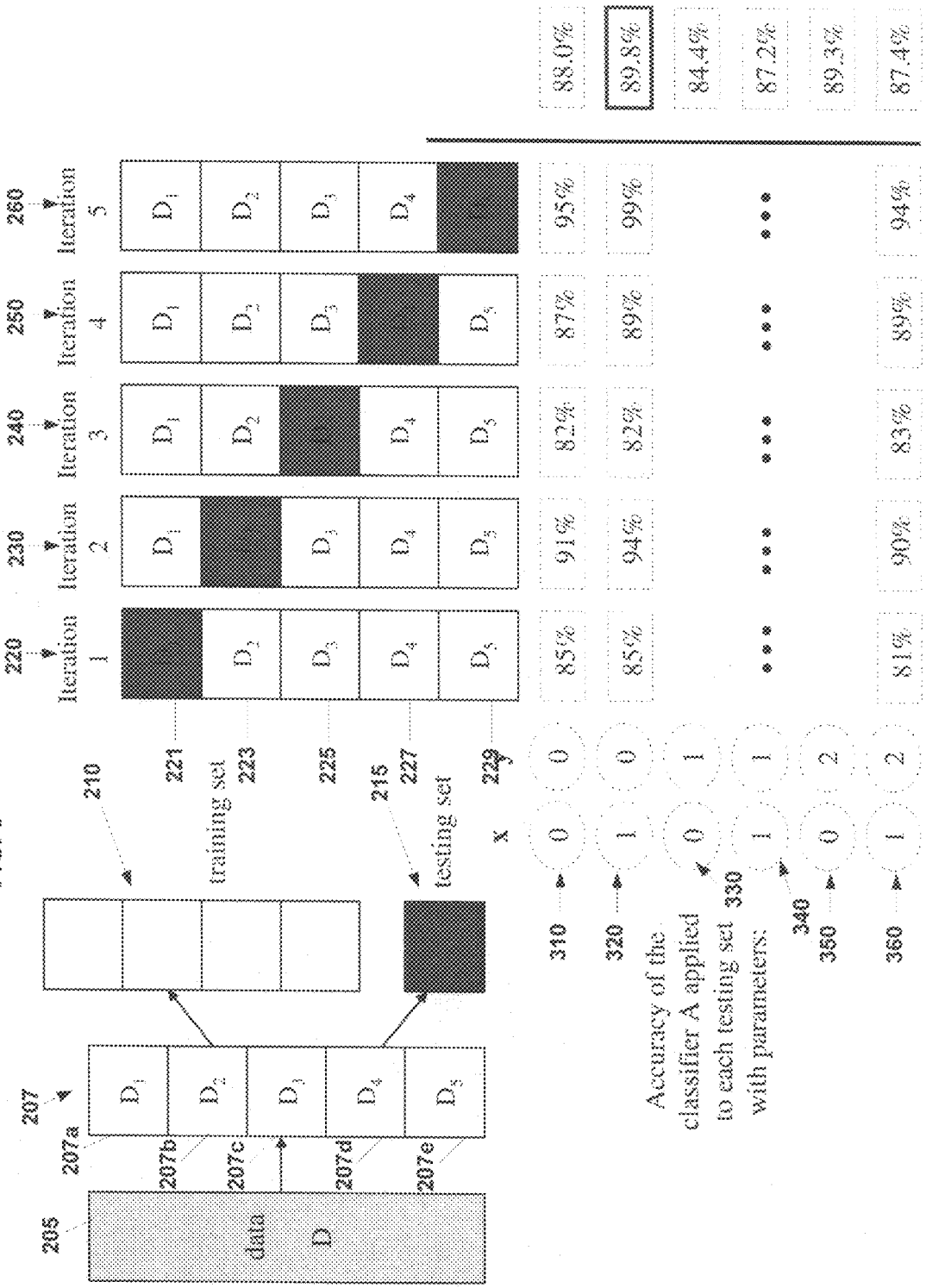
FIG. 3 is a block diagram of how a data set may be split into training sets/subsets and a testing set/subset for a 5-fold cross-validation for selection of a classifier model using the data set and multiple model parameters, in accordance with one or more embodiments of the present invention.

To estimate the optimal value of ac, cross-validation may be used as follows: The performance P(i) of classifier A trained with parameter $\alpha_i$ is estimated for i=1, . . . , m by cross-validation. The final model is built by training A on all available data D using the parameter $\alpha_j$, where j=argmax P(i) for i=1,..., m. FIG. 3 is a block diagram of how a data set may be split into training sets/subsets and a testing set/subset for a 5-fold cross-validation selection of a classifier model using the data set and multiple model parameters, in accordance with one or more embodiments of the present invention. In FIG. 3 cross-validation is used only for model selection and it does not provide an unbiased performance estimate for the final model. This process may be referred to as optimal model selection or cross-validation for model selection. As seen in FIG. 3, a different set of parameters, x and y, are associated with classifier A. In fact, in the example in FIG. 3, six (6) different sets of parameters 310, 320, 330, 340, 350, 360 are used with classifier A, and the second set {1, 0} 320 resulted in the best 5-fold cross-validation accuracy (89.8%) 370. Therefore, classifier A is trained on the entire dataset D 205 using the second parameter set 320 to determine the final classification model.

Figure 4:
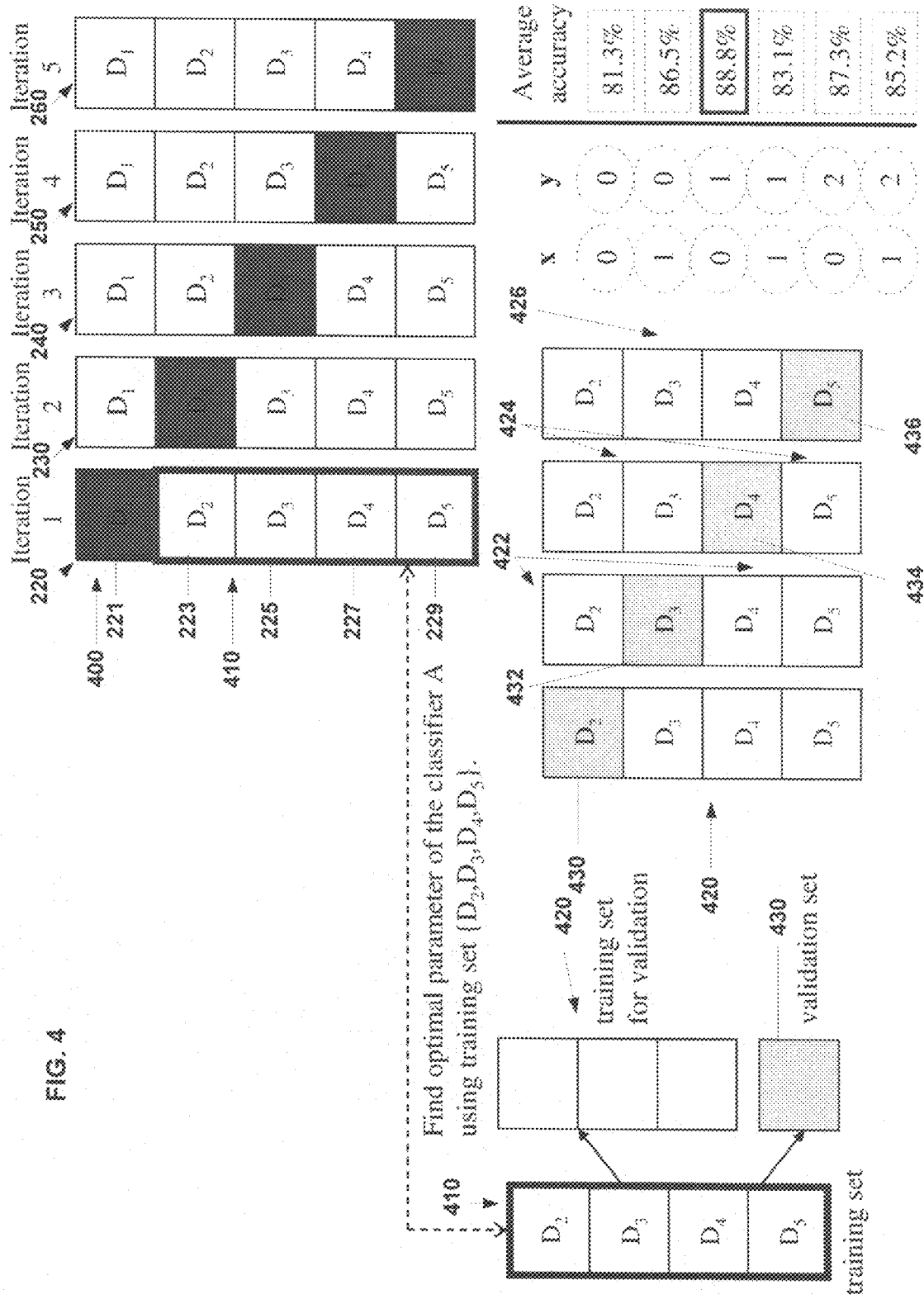
FIG. 4 is a block diagram of how a data set may be separately split into training sets/subsets and a testing set/subset for a nested 5-fold cross-validation for performance estimation of a selected classification model using an optimal parameter for the classification model, in accordance with one or more embodiments of the present invention.

Unbiased Performance Estimation. In order to combine optimal model selection and unbiased performance estimation, the cross-validation for model selection may be "nested" inside the cross-validation for performance estimation to obtain a nested cross-validation procedure. FIG. 4 is a block diagram of how a data set may be separately split into training sets/subsets and a testing set/subset for a nested 5-fold cross-validation performance estimation of a selected classification model using an optimal parameter for the classification model, in accordance with one or more embodiments of the present invention. As seen in FIG. 4, a training set $\{D_2, D_3, D_4, D_5\}$ 410 (223, 225, 227, 229) from Iteration 1 220 is used to determine a 4-fold cross validation accuracy for Iteration 1 220. Testing set $\{D_1\}$ 400 from Iteration 1 220 is reserved for later use, which was first data subset $\{D_1\}$ 221 and used in the 5-fold cross-validation for model selection described in FIG. 3. In FIG. 4, training set 410 may be divided into a first training set for validation 420 having 3 separate datasets $\{D_3, D_4, D_5\}$ and a validation set 430 having a single dataset $\{D_2\}$. Training set 410 may also be divided into a second training set for validation 422 $\{D_2, D_4, D_5\}$ and a second validation set 432 $\{D_3\}$, a third training set for validation 424 $\{D_2, D_3, D_5\}$ and a third validation set 434 $\{D_4\}$, and a fourth training set for validation 426 $\{D_2, D_3, D_4\}$ and a fourth validation set 436 $\{D_5\}$ The optimal parameter configuration of classifier A for Iteration 1 is determined using the above training sets for validation 420, 422, 424, 426, first x, y parameter set 310, and validation sets 430, 432, 434, 436. Classifier A is then trained on training set 410 $\{D_2, D_3, D_4, D_5\}$ using the determined optimal parameter set and tested using testing set 400 $\{D_1\}$ to obtain an optimal performance for classifier A for Iteration 1 220 using first x, y parameter set 310. This value is then saved to be averaged with other optimal performances for Iterations 2, 3 and 4 using first x, y parameter set 310. The above is repeated for Iteration for each parameter set.

The above process is also performed for Iteration 2 through Iteration 5, 230, 240, 250, 260, respectively, and an average performance over all of the Iterations for each parameter set is obtained. A general algorithm for performing the process of FIG. 4 may be stated as:

(1) Find an optimal parameter configuration of classifier A using the training set from Iteration i, for each iteration, where for i=1 to N, as shown in FIG. 4, the training set includes $\{D_2, D_3, D_4, D_5\}$ for Iteration 1;

(2) Train classifier A on a training set for validation ($\{D_2, D_3, D_4, D_5\}$ for Iteration 1) with its optimal parameter and test it on the testing set ($\{D_1\}$ for Iteration 1) for this iteration i to obtain a performance measure;

(3) Iterate through (1) and (2) for each Iteration's training and testing sets; and (4) Return an average performance measure for all N Iterations (from (2)).

In the example shown in FIG. 4, third parameter set {0, 1} 330 had the highest average accuracy for Iteration 1 (88.8%), so the most accurate model for Iteration 1 was obtained using third parameter set {0, 1} 330.

Because the optimized classifier is evaluated each time on a testing set that was not used for learning, the resulting performance estimate is unbiased. (See, Dudoit S and van der Laan M J, "Asymptotics of Cross-Validated Risk Estimation in Model Selection and Performance Assessment.", U.C. Berkeley Division of Biostatistics Working Paper Series, Working Paper 126, Feb. 5, 2003; and Scheffer T, "Error Estimation and Model Selection.", Ph.D. thesis, Technischen Universität Berlin, School of Computer Science, 1999.)

In general, the algorithm described above in relation to FIG. 4 avoids the following common pitfall in estimating the performance of a diagnostic model produced by a parametric classifier. Quite often, the procedure in FIG. 3 may identify the best parameter values from which to build the final model. However, the best cross-validation performance P(j), where j=argmax P(i) for i=1,..., m is often reported as an estimate of performance of the final model, instead of applying a second cross-validation loop over the whole model selection procedure, as in FIG. 4. For a sufficiently large number of attempted parameter values, a model is likely to be found that by chance alone provides a high estimate of cross-validation performance. Unfortunately, the smaller the available data sample is, and the more complex the models that the classifier can build are, the more acute the problem becomes. In contrast, the described nested cross-validation protocol will be able to identify whether the model selection procedure is selecting values that by accident produce models that perform well on the test sets, or indeed the selected model generalizes well to unseen cases.

Using Domain Knowledge to Restrict the Combinatorial Space of Models. In general, embodiments of the present invention may limit the combinatorial space of all possible classification models by design so that computer-based efficient search of that space is feasible in small amounts of time. To determine the best way to constraint the space of models to be examined, an algorithmic evaluation in the application domain may be performed. For example, for biomedically-oriented supervised analysis of microarray data as implemented in an embodiment of the present invention a large-scale comparative study was conducted (see, Statnikov A, Aliferis C F, Tsamardinos I, "Methods for Multi-category Cancer Diagnosis from Gene Expression Data: A Comprehensive Evaluation to Inform Decision Support System Development.", Medinfo, 2004.) with algorithms and datasets listed in Appendix B and Appendix C, respectively. In summary, the following was concluded:

For multi-category classification of cancer from microarray gene expression data, Support Vector Machines (SVMs) are the best performing family among the tested algorithms outperforming K-Nearest Neighbors, Backpropagation Neural Networks, Probabilistic Neural Networks, Decision Trees, and Weighted Voting classifiers to a statistically significant degree;

Among multi-category Support Vector Machines, the best performing techniques are: one-versus-rest, the method by Weston and Watkins, and the method by Crammer and Singer;

The diagnostic performance can be moderately improved for SVMs and significantly improved for the non-SVM methods by gene selection;

Ensemble classification does not improve performance of the best non-ensemble diagnostic models;

The obtained results favorably compare with the primary literature on the same datasets.

Integrating Domain Knowledge and Processes for Optimal Model Selection and Unbiased Model Performance Estimation. In embodiments of the present invention, processes for optimal model selection and unbiased performance estimation may be maintained with the domain knowledge of the best performing methodologies obtained during an extensive algorithmic evaluation, as described above. Given an input dataset, a software implementation of the present invention may automatically perform one of the following tasks:

I. Generate a classification model by optimizing the parameters of classification and variable selection algorithms as well as the choice of the classifier and variable selection methods using cross-validation for model selection;

II. Estimate classification performance of the optimized model by nested cross-validation;

III. Perform tasks I and II, i.e. generate a classification model and estimate its performance;

IV. Apply an existing model to a new set of subjects.

Note that in tasks I, II, and III selection of variables (for example, biomarkers) is performed as part of the model selection process and may constitute part of the invention's output.

In order to execute the tasks mentioned above, the user may select the validation method (N-fold cross-validation or leave-one-out cross-validation), the algorithm(s) to be used for classification, variable selection, and normalization, and the ranges of parameters over which optimization should take place. Appendix D summarizes all implemented algorithms in the present software embodiment of the invention.

The new method provides an intuitive data analysis protocol that abstracts the supervised analysis of data and does not require users to be knowledgeable about that field. The protocol consists of discrete serial steps each considering options and corresponding to a specific sub-task of analysis:

For tasks I-III: dataset specification, cross-validation design, normalization, classification, variable selection, performance estimation, logging, report generation, and execution of analysis.

For task IV: dataset specification, performance estimation, logging, report generation, and execution of analysis.

For example in the present software system embodiment, the method implements the data analysis process by means of an intuitive wizard-like user interface with several steps corresponding precisely to the stages of analysis described above. The software system implements a client-server architecture consisting of a computational engine and an interface client. The computational engine is separated from the client and consists of intercommunicating functional units corresponding to different aspects of analysis. Upon completion of analysis, a detailed report is generated with links to system inputs and outputs as well as links to resources with information on selected genes.

In accordance with an embodiment of the present invention, data input and execution in the software system may be implemented using a set of screens as shown in FIGS. 5-14.

Figure 5:
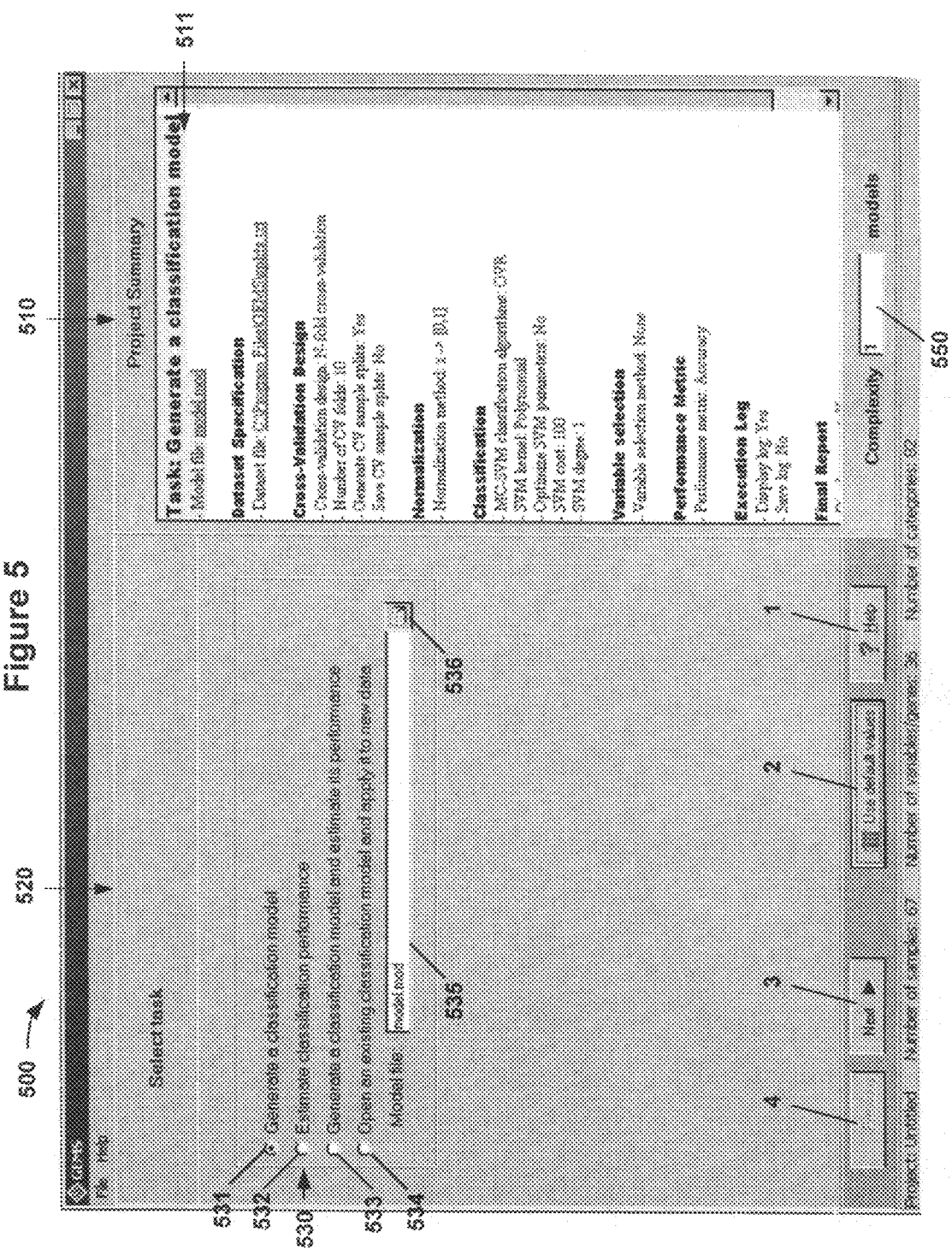
FIG. 5 is a screen shot of a task selection screen for selecting which task to perform from a list of tasks associated with the model, in accordance with one or more embodiments of the present invention.

FIG. 5 is a screen shot of a task selection screen for selecting which task to perform from a list of tasks associated with the model, in accordance with one or more embodiments of the present invention. In FIG. 5, an example screen 500 includes a project summary section 510 and user interaction section 520 with a user task input subsection 530. Project summary section 510 may include the tasks and elements that are available in the model. For example, in project summary section 510 task element 511 is highlighted and displays "Task: Generate a classification model, Model File: model.mod", which is displayed as a result of the user selecting the "Generate a classification model" check button 531. Alternative task options that are available include "Estimate classification performance" check button 532, "Generate a classification model and estimate its performance" check button 533, and "Open an existing classification model and apply it to new data" check button 534. "Open an existing classification model and apply it to new data" check button 534 has associated with it a model file input line 535 through which a user can select the model file to be used by the model to generate the classification. To aid in selecting which model is used, a folder radio button 536 is provided at the end of model file input line 535 to permit the user to browse through the available directories/folders and select an appropriate file.

In FIG. 5, help information may be accessed by selecting (e.g., left clicking on and/or pressing the "H" key) a "? Help" radio button 1. In addition, a "Use default values" radio button 2 may be selected to use a predefined set of default task values, and a "Next" radio button 3 may be selected to advance to the next screen. Although a "Previous" radio button 4 is shown, it is not active on this screen, since this is the first screen in the series. Screen 500 may also include a complexity input window 550 in which a value for the number of different models used in determining the optimal model may be specified, with 1 model being the lowest complexity and values greater than one being increasingly more complex.

Figure 6:
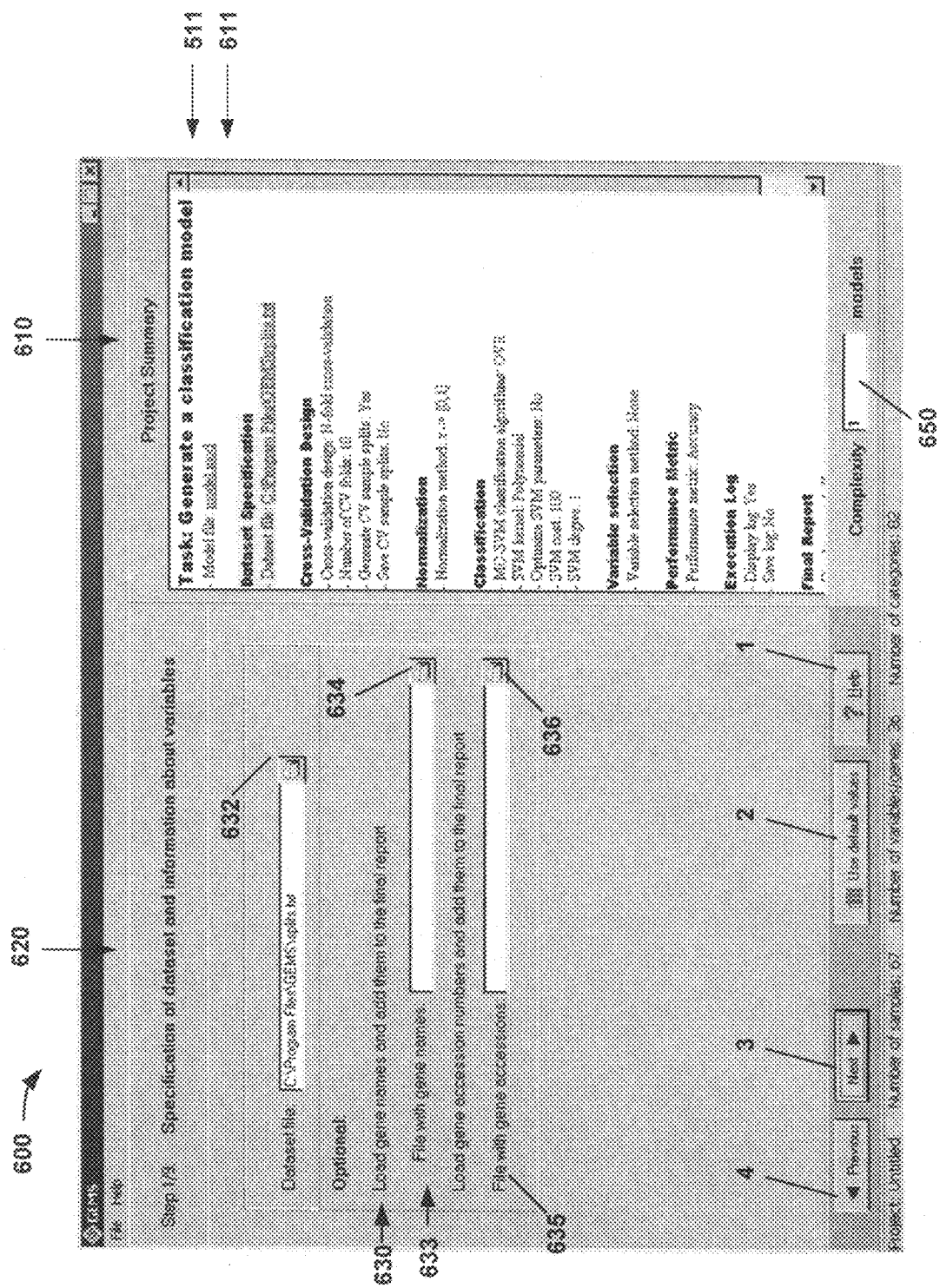
FIG. 6 is a screen shot of a dataset and variable information screen for specifying which dataset to use and optional detailed information about the dataset, in accordance with one or more embodiments of the present invention.

FIG. 6 is a screen shot of a dataset and variable information screen for specifying which dataset to use and optional detailed information about the dataset, in accordance with one or more embodiments of the present invention. Similar to FIG. 5, in FIG. 6, an example screen 600 includes a project summary section 610 and user interaction section 620 with a user dataset input subsection 630. Project summary section 610 may include the tasks and elements that are available in the model. For example, in project summary section 610 dataset specification element 611 is highlighted and displays "Dataset Specification, Dataset File: C:\Program_Files\GEMS\splits.txt", which is displayed as a result of the user selecting that file in dataset file window 631. A dataset folder radio button 632, which is associated with dataset file window 631 may be used to aid in the selection of the desired dataset file. Optional dataset inputs include "Load gene names and add them to the final report, File with gene names:" window 633, and "Load gene accession numbers and add them to the final report, File with gene accessions:" window 635. A gene name folder radio button 634, which is associated with window 633 may be used to aid in the selection of the desired gene name file, and a gene accession folder radio button 636, which is associated with window 635 may be used to aid in the selection of the desired gene accession file.

In FIG. 6, help information may be accessed by selecting (e.g., left clicking on and/or pressing the "H" key) "? Help" radio button 1. In addition, a "Use default values" radio button 2 may be selected to use a predefined set of default task values, a "Next" radio button 3 may be selected to advance to the next screen, and a "Previous" radio button 4 may be selected to go back to the previous screen. Screen 600 may also include a complexity input window 650 in which a value for the number of different models used in determining the optimal model may be specified, with 1 model being the lowest complexity and values greater than one being increasingly more complex.

Figure 7:
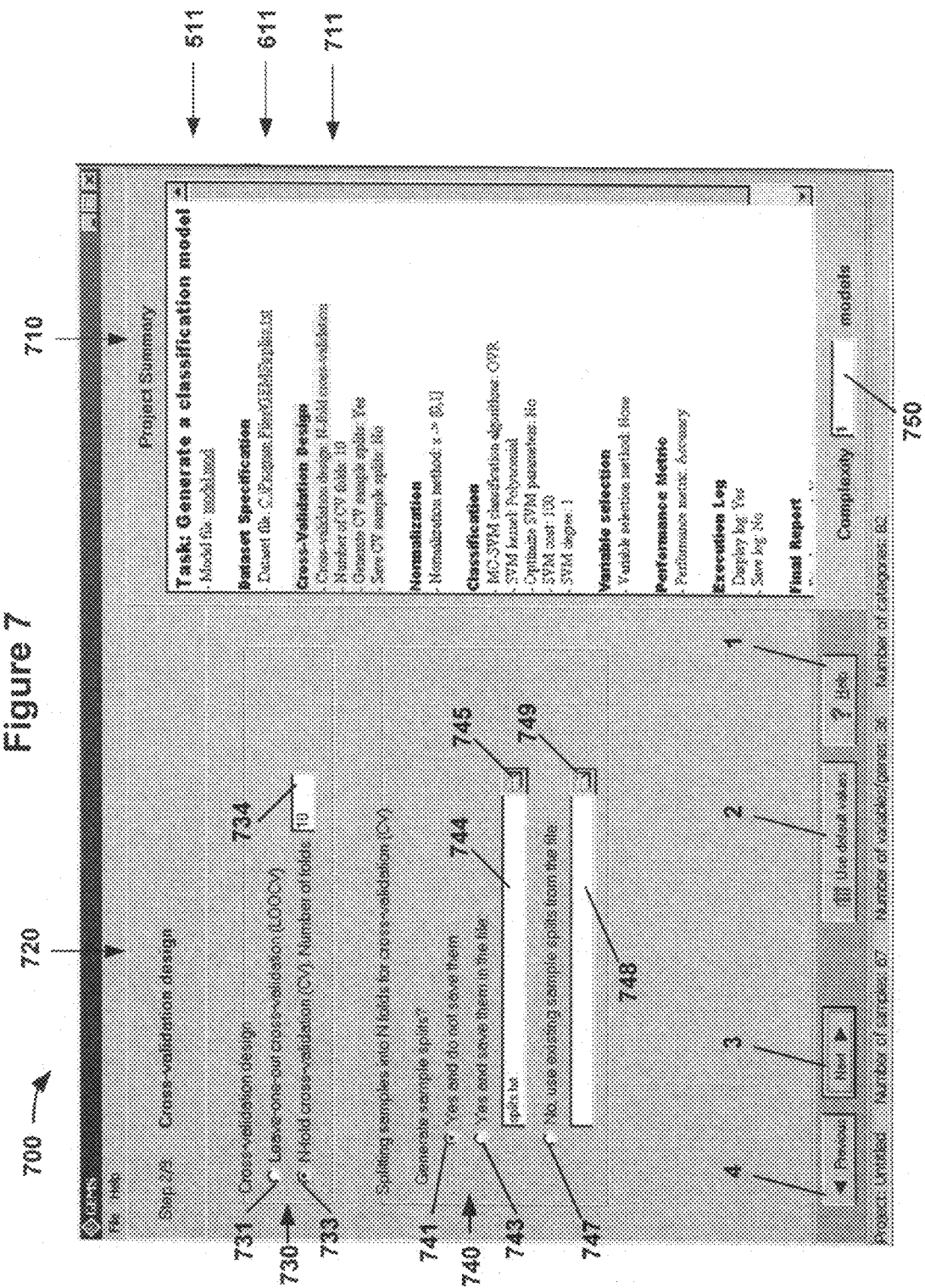
FIG. 7 is a screen shot of a cross-validation design screen for selecting which type of cross-validation design to use in determining the best, in accordance with one or more embodiments of the present invention.

FIG. 7 is a screen shot of a cross-validation design screen for selecting which type of cross-validation design to use in determining the best, in accordance with one or more embodiments of the present invention. Similar to FIGS. 5 and 6, in FIG. 7, an example screen 700 includes a project summary section 710 and user interaction section 720 with multiple user cross-validation design input subsections 730, 740. Project summary section 710 may include the tasks and elements that are available in the model. For example, in project summary section 710 cross-validation design element 711 is highlighted and displays information on which cross-validation design is to be used, the number of cross-validation folds, whether to generate cross-validation sample splits, and whether to save the cross-validation splits. All of this information is displayed as a result of the user inputs in cross-validation subsection 730 and splitting samples into N folds for cross-validation subsection 740. A leave-one-out cross-validation (LOOCV) check button 731, and an N-fold cross-validation check button 733 are associated with cross-validation subsection 730 and permit the user to specify the cross-validation design inputs. Splitting samples into N folds for cross-validation subsection 740 includes a "yes and do not save them" check button 741, a "yes and save them in the file:" check button 743, and a "no, use existing sample splits from the file:" check button 747 to specify whether the splits are generated or pulled from an existing file. Associated with "yes and save them in the file:" check button 743 is a save split file name window 744 and a split file name folder radio button 745, which can be used to specify the file name and location of the split file. Associated with "no, use existing sample splits from the file:" check button 747 is an existing split file name window 748 and an existing split file name folder radio button 749, which can be used to select the existing split file name and location of the split file that is to be used.

In FIG. 7, help information provided may be accessed by selecting (e.g., left clicking on and/or pressing the "H" key) "? Help" radio button 1. In addition, a "Use default values" radio button 2 may be selected to use a predefined set of default task values, a "Next" radio button 3 may be selected to advance to the next screen, and a "Previous" radio button 4 may be selected to go back to the previous screen. Screen 700 may also include a complexity input window 750 in which a value for the number of different models used in determining the optimal model may be specified, with 1 model being the lowest complexity and values greater than one being increasingly more complex.

Figure 8:
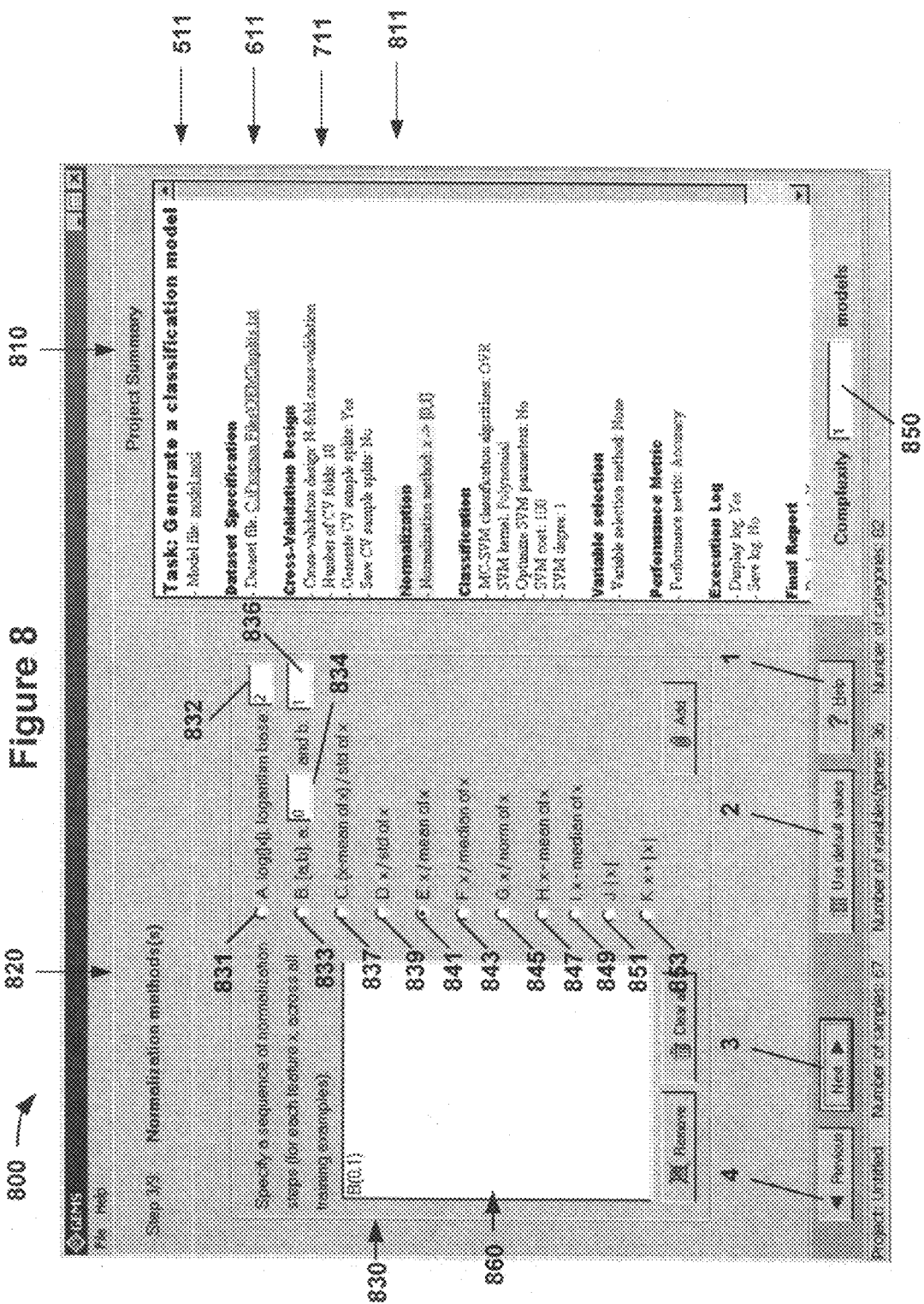
FIG. 8 is a screen shot of a normalization method selection screen for specifying, which, if any, sequence of normalizations are to be applied across all training sets, in accordance with one or more embodiments of the present invention.

FIG. 8 is a screen shot of a normalization method selection screen for specifying, which, if any, sequence of normalizations are to be applied based on all training sets, in accordance with one or more embodiments of the present invention. In FIG. 8, an example screen 800 includes a project summary section 810 and user interaction section 820 with a user normalization method input subsection 830. Project summary section 810 may include the tasks and elements that are available in the model. For example, in project summary section 810 normalization element 811 is highlighted and displays "Normalization method: x=>[0,1]", which is displayed as a result of the user selections in user normalization method input subsection 830. In user normalization method input subsection 830 multiple check buttons are available for selection and one or more may be selected for used in normalizing the model. For example, the check buttons may include "A.log(|x|)," check box 831 with "logarithm base:" entry window 832 to permit the user to enter the base of the logarithm to be used; "B.[a,b]," check box 833 with "a:" entry window 834 and "b:" entry window 836 to permit the user to enter values for a and b; "C.(x-mean of x)/std of x" check box 837; "D.x/std of x" check box 839; "E.x/mean of x" check box 841; "F.x/median of x" check box 843; "G.x/norm of x" check box 845; "H.x—mean of x" check box 847; I.X—median of x" check box 849; "J.|x|" check box 851; and "K.x +|x|" check box 853. A display window 860 to display the sequence of normalization steps that are to be performed based on all training examples is also included in user normalization method input subsection 830. A user may select one or more of the check boxes and when the desired mix of normalization methods is achieved, the user may select "Add" radio button 861 to put the selected normalization methods into display window 860. "Clear all" radio button 863 may be used to clear all normalization methods shown in display window 860 and "Remove" radio button 864 may be used to clear a single, specifically selected on of the normalization methods shown in display window 860.

In FIG. 8, help information may be accessed by selecting (e.g., left clicking on and/or pressing the "H" key) "? Help" radio button 1. In addition, a "Use default values" radio button 2 may be selected to use a predefined set of default task values, a "Next" radio button 3 may be selected to advance to the next screen, and a "Previous" radio button 4 may be selected to go back to the previous screen. Screen 800 may also include a complexity input window 850 in which a value for the number of different models used in determining the optimal model may be specified, with 1 model being the lowest complexity and values greater than one being increasingly more complex.

Figure 9:
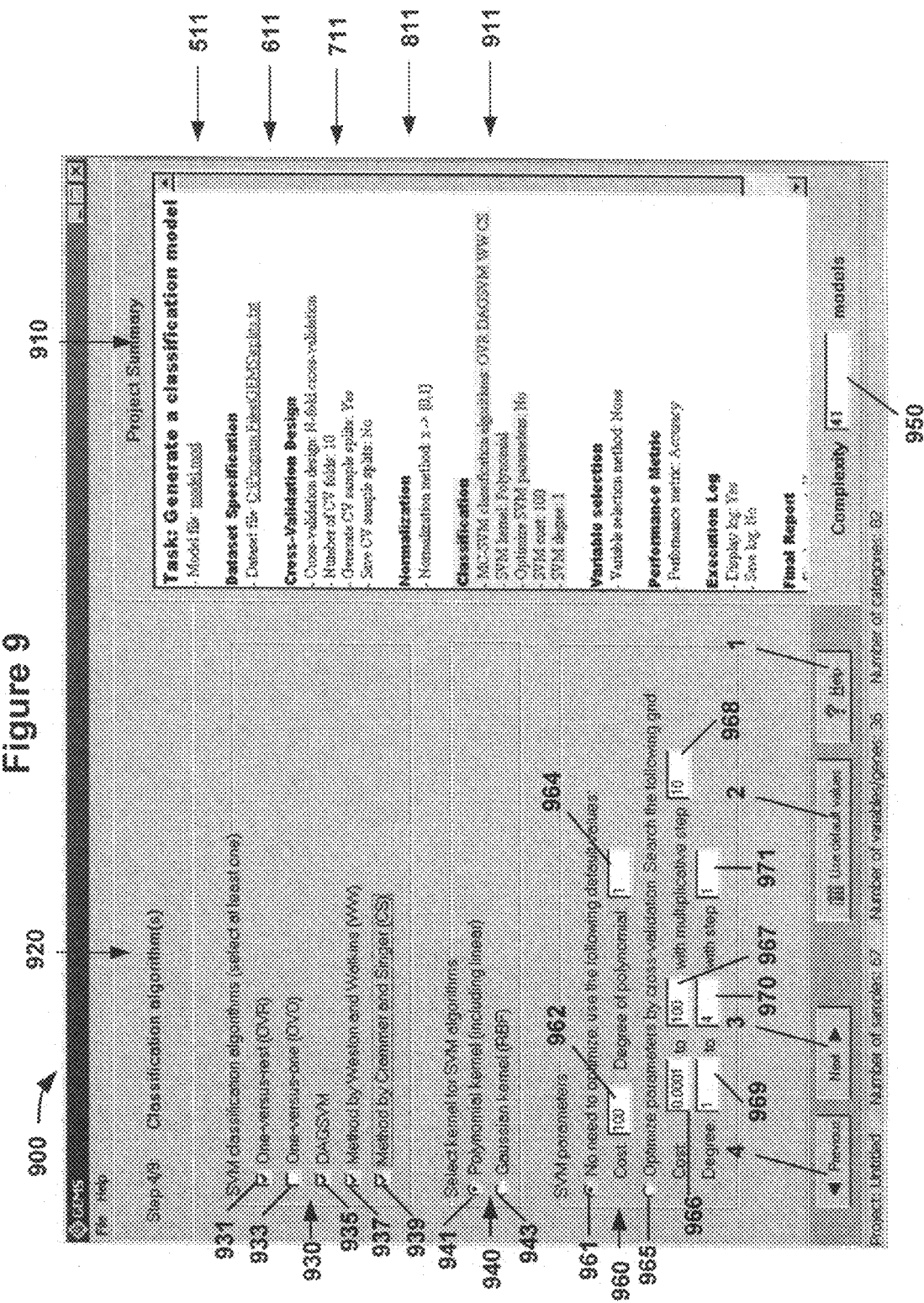
FIG. 9 is a screen shot of a classification algorithm selection screen for selecting which classification algorithms and parameters will be used to determine the best classification model, in accordance with one or more embodiments of the present invention.

FIG. 9 is a screen shot of a classification algorithm selection screen for selecting which classification algorithms and parameters will be used to determine the best classification model, in accordance with one or more embodiments of the present invention. In FIG. 9, an example screen 900 includes a project summary section 910 and user interaction section 920 with a SVM classification algorithm selection subsection 930, a select kernel for SVM algorithm selection subsection 940, and a SVM parameters selection/input subsection 960. Project summary section 910 may include the tasks and elements that are available in the model. For example, in project summary section 910 classification element 911 is highlighted and displays information on which MC-SVM classification algorithms are to be used, which SVM kernel is to be used, whether to optimize the SVM parameters, and what, if any, parameters are to be optimized and at what cost and degree.

In SVM classification algorithm selection subsection 930, for example, the check buttons may include a "One-versus-rest (OVR)" check box 931; a "One-versus-one (OVO)" check box 933; a "DAGSVM" check box 935; a "Method by Weston and Watkins (WW)" check box 937; and a "Method by Crammer and Singer (CS)" check box 939. In select kernel for SVM algorithm selection subsection 940, for example, the check buttons may include a "Polynomial kernel (including linear)" check box 941; and a "Gaussian kernel (RBF)" check box 943. In SVM parameters selection/input subsection 960, for example, the check buttons and input windows may include a "No need to optimize" check button 961 with which may be associated a "Cost" input box 961 to input a cost, for example, 100, and a "Degree of polynomial:" input box 962 to input a degree, for example, 1. SVM parameters selection/input subsection 960 may also include an "Optimize parameters by cross-validation" check button with which may be associated "Cost" range input boxes 966, 967 to permit a user to enter a cost range, a "multiplicative step" input box 968 to permit the user to enter a multiplier for the costs; "Degree" range input boxes 969, 970 to permit the user to enter a degree range and a "Step" input box 971 to permit the user to enter a step for the degree of a kernel.

In FIG. 9, help information may be accessed by selecting (e.g., left clicking on and/or pressing the "H" key) "? Help" radio button 1. In addition, a "Use default values" radio button 2 may be selected to use a predefined set of default task values, a "Next" radio button 3 may be selected to advance to the next screen, and a "Previous" radio button 4 may be selected to go back to the previous screen. Screen 900 may also include a complexity input window 950 in which a value for the number of different models used in determining the optimal model may be specified, with 1 model being the lowest complexity and values greater than one being increasingly more complex.

Figure 10:
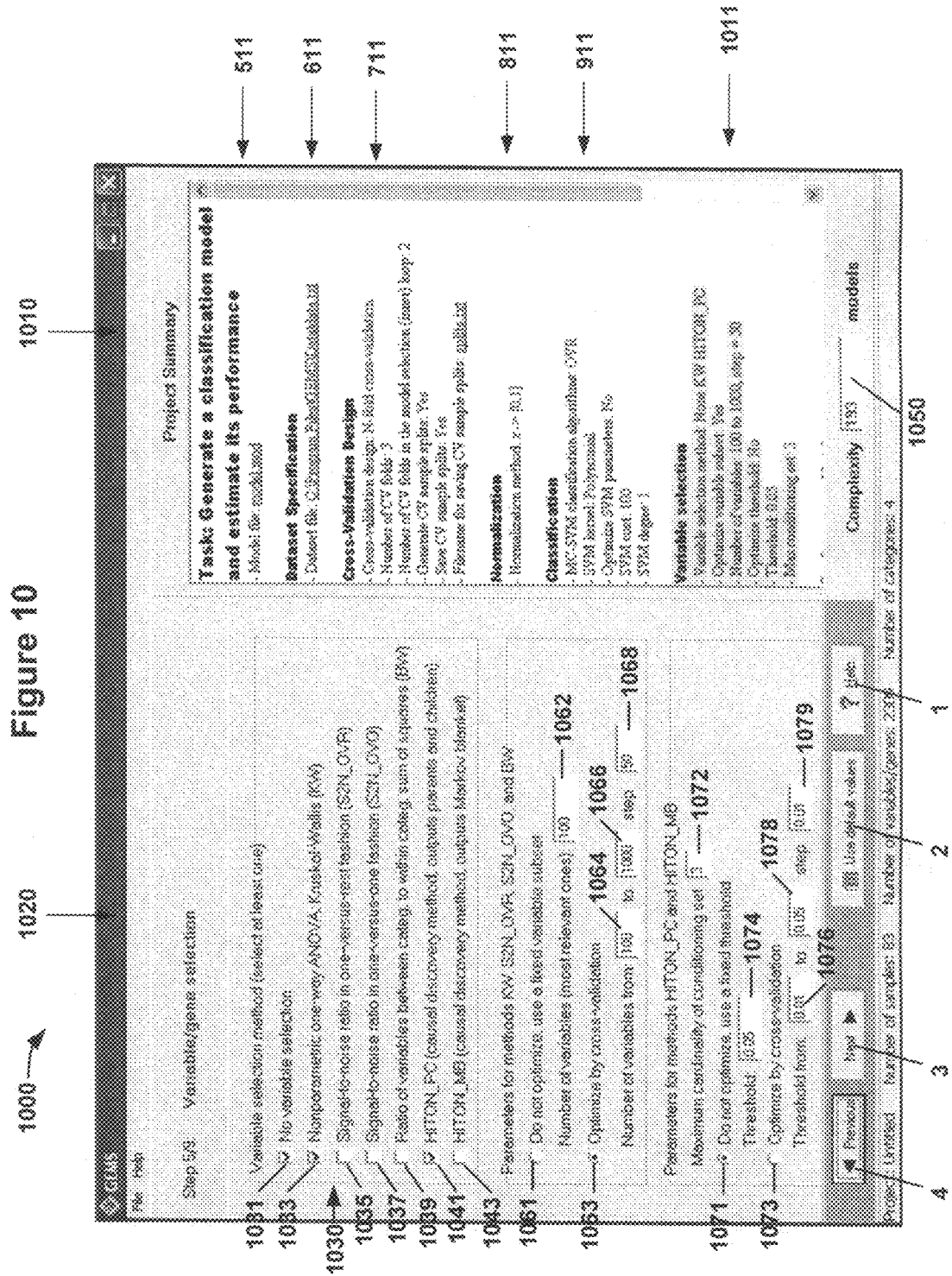
FIG. 10 is a screen shot of a variable/gene selection screen for selecting, one or more methods of how variables are selected, in accordance with one or more embodiments of the present invention.

FIG. 10 is a screen shot of a variable/gene selection screen for selecting one or more methods of how variables are selected, in accordance with one or more embodiments of the present invention. In FIG. 10, an example screen 1000 includes a project summary section 1010 and user interaction section 1020 with a variable/gene selection method selection subsection 1030, a KW-S2N_OVR-S2N_OVO-BW methods parameters selection subsection 1060, and a HITON methods parameters selection subsection 1070. Although, KW-S2N_OVR-S2N_OVO-BW methods parameters selection subsection 1060 and HITON methods parameters selection subsection 1070 may only be displayed if one or more of their methods are selected. Project summary section 1010 may include the tasks and elements that are available in the model. For example, in project summary section 1010 variable selection element 1011 is highlighted and displays information on which variable selection methods are to be used, as selected in variable/gene selection method selection subsection 1030. In variable selection method selection subsection 1030, for example, the check buttons may include a "No variable selection" check box 1031; a "Nonparametric one-way ANOVA: Kruskal-Wallis (KW)" check box 1033; a "Signal-to-noise ratio in one-versus-rest fashion (S2N_OVR)" check box 1035; a "Signal-to-noise ratio in one-versus-one fashion (S2N_OVO)" check box 1037; a "Ratio of variables between categ. to within categ. sum of squares (BW)" check box 1039; a "HITON_PC (causal discovery method: outputs parents and children)" check box 1041; and a "HITON_MB (causal discovery method: outputs Markov blanket)" check box 1043. At least one of the above selection methods must be selected, which includes the "No variable selection" check box 1031, and also permits the selection of more than one of the remaining methods when variable selection is to occur.

In FIG. 10, KW-S2N_OVR-S2N_OVO-BW methods parameters selection subsection 1060 the check boxes may include a "Do not optimize, use a fixed variable subset" check box 1061 and an "Optimize by cross-validation" check box 1063. Associated with check box 1061 is a "Number of variables (most relevant ones):" input box 1062 in which the number of most relevant variables may be entered. Similarly, associated with check box 1063 are several input boxes, a "Number of variables from:" lower bound input box 1064, a "Number of variables from:" upper bound input box 1066, and a "step" input box 1068, which are each used to specify the range of the number of variables and the step function to be used for the cross-validation optimization.

In FIG. 10, HITON methods parameters selection subsection 1070 the check boxes may include a "Do not optimize, use a fixed threshold" check box 1071 and an "Optimize by cross-validation" check box 1073. A "Maximum cardinality of conditioning set" input box 1072 may be included, which may be used to receive the maximum cardinality value for the conditioning set. Associated with check box 1071 is a "Threshold" input box 1074 in which the fixed threshold to be used may be entered. Similarly, associated with check box 1073 are several input boxes, a "Number of variables from:" lower bound input box 1076, a "Number of variables from:" upper bound input box 1078, and a "step" input box 1079, which are each used to specify the range of the number of variables and the step function to be used for the cross-validation optimization.

In FIG. 10, help information provided may be accessed by selecting (e.g., left clicking on and/or pressing the "H" key) "? Help" radio button 1. In addition, a "Use default values" radio button 2 may be selected to use a predefined set of default task values, a "Next" radio button 3 may be selected to advance to the next screen, and a "Previous" radio button 4 may be selected to go back to the previous screen. Screen 1000 may also include a complexity input window 1050 in which a value for the number of different models used in determining the optimal model may be specified, with 1 model being the lowest complexity and values greater than one being increasingly more complex.

Figure 11:
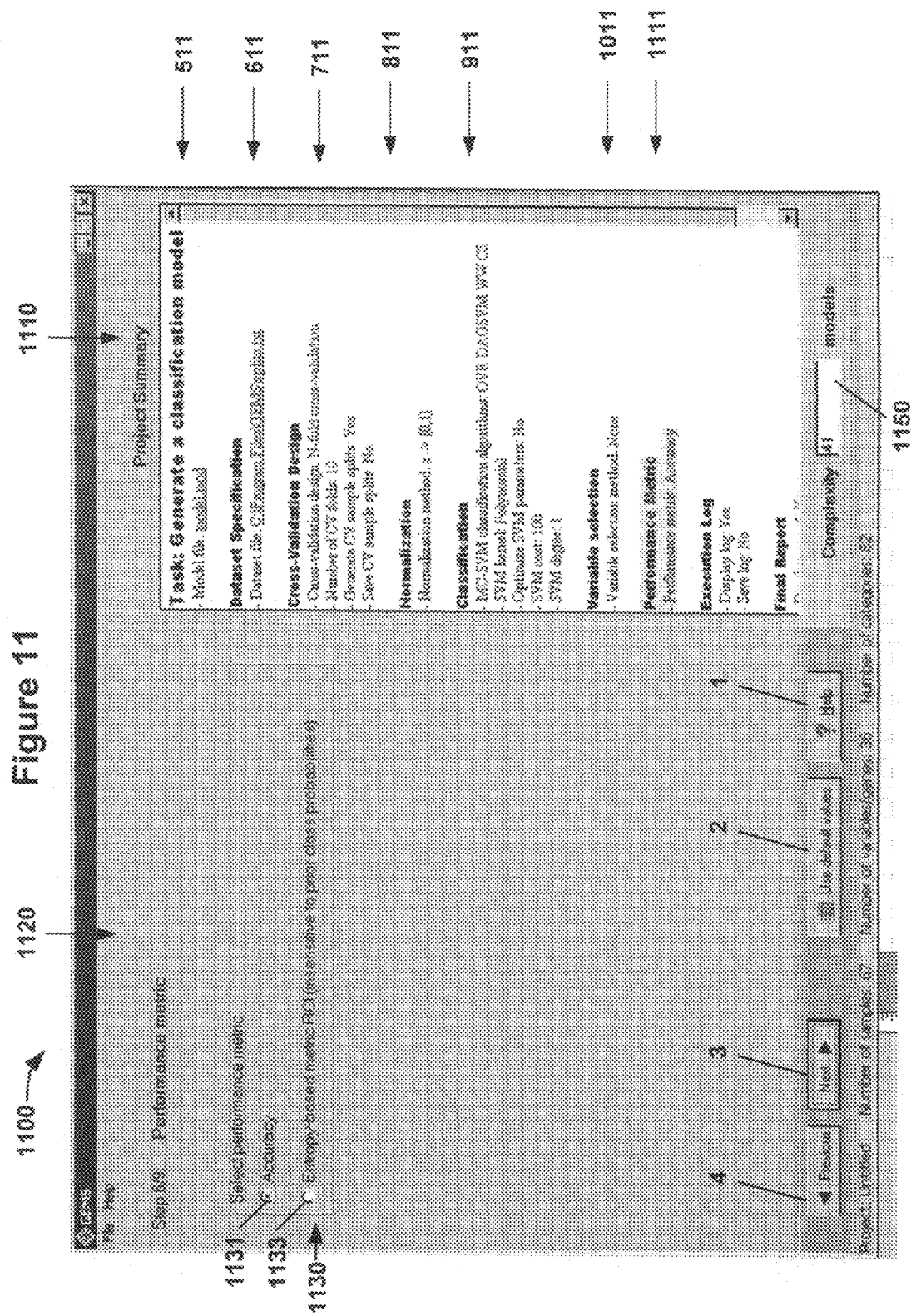
FIG. 11 is a screen shot of a performance metric selection screen for selecting a metric for how performance will be evaluated, in accordance with one or more embodiments of the present invention.

FIG. 11 is a screen shot of a performance metric selection screen for selecting a metric for how performance will be evaluated, in accordance with one or more embodiments of the present invention. In FIG. 11, an example screen 1100 includes a project summary section 1110 and user interaction section 1120 with a performance metric selection subsection 1130. Project summary section 1110 may include the tasks and elements that are available in the model. For example, in project summary section 1110 performance metric element 1111 is highlighted and displays information on which performance metric is to be used, as selected in performance metric selection subsection 1130. In performance metric selection subsection 1130, for example, the check buttons may include an "Accuracy" check box 1131 and an "Entropy-based metric RCI (insensitive to prior class probabilities)" check box 1133. If the classification task has only two categories, an additional check button "Area under ROC curve" may be included, which may allow the user to select area under ROC performance metric.

In FIG. 11, help information may be accessed by selecting (e.g., left clicking on and/or pressing the "H" key) "? Help" radio button 1. I In addition, a "Use default values" radio button 2 may be selected to use a predefined set of default task values, a "Next" radio button 3 may be selected to advance to the next screen, and a "Previous" radio button 4 may be selected to go back to the previous screen. Screen 1100 may also include a complexity input window 1150 in which a value for the number of different models used in determining the optimal model may be specified, with 1 model being the lowest complexity and values greater than one being increasingly more complex.

Figure 12:
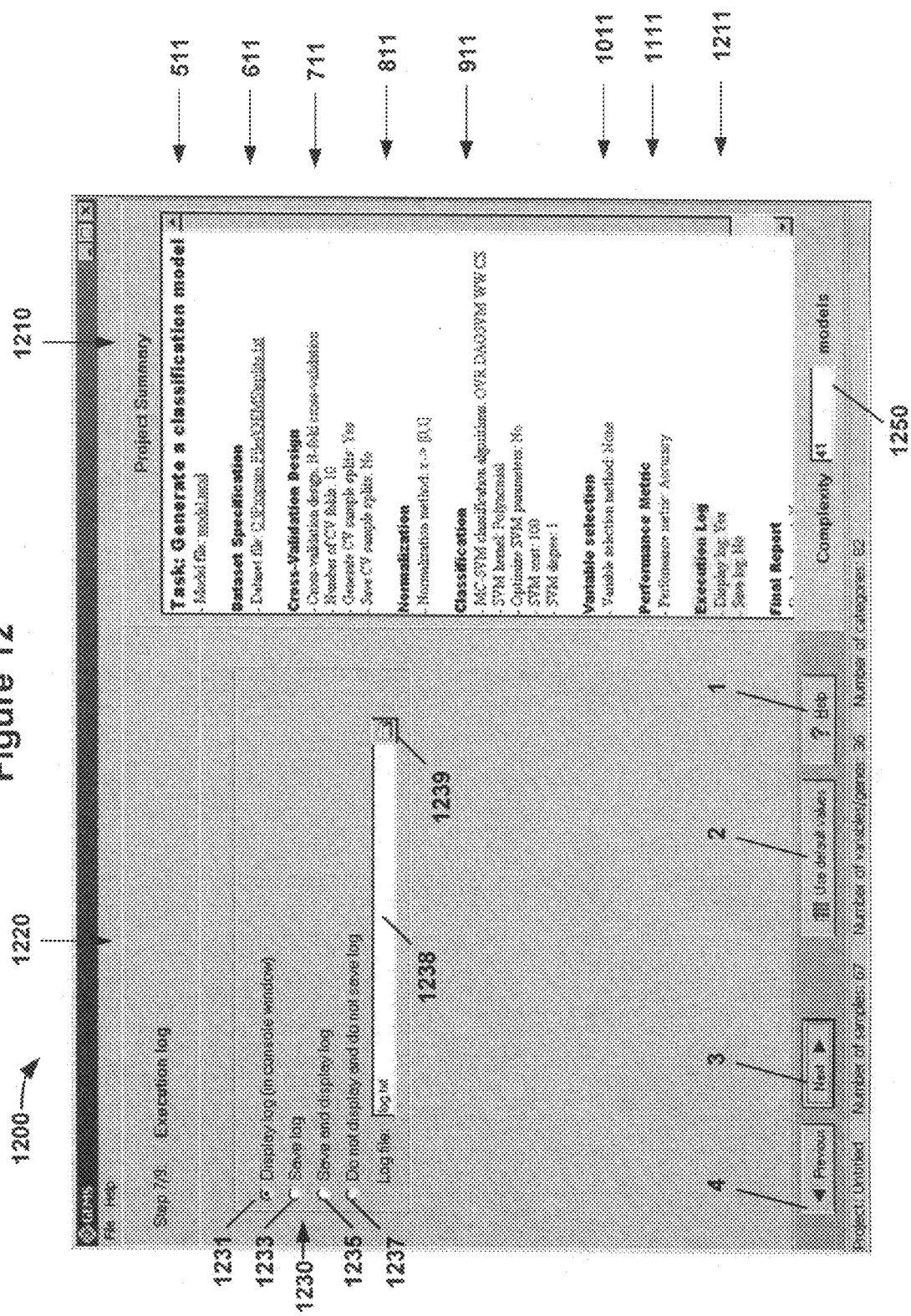
FIG. 12 is a screen shot of an execution log selection screen for selecting how the execution log of the model will be displayed and/or saved, in accordance with one or more embodiments of the present invention.

FIG. 12 is a screen shot of an execution log selection screen for selecting how the execution log of the model will be displayed and/or saved, in accordance with one or more embodiments of the present invention. In FIG. 12, an example screen 1200 includes a project summary section 1210 and user interaction section 1220 with an execution log option selection subsection 1230. Project summary section 1210 may include the tasks and elements that are available in the model. For example, in project summary section 1210 execution log element 1211 is highlighted and displays information on which execution log option is to be used to display and/or save the log file after execution of the model, as selected in execution log option selection subsection 1230. In execution log option selection subsection 1230, for example, the check buttons may include a "Display log (in console window)" check box 1231; a "Save log" check box 1233; a "Save and display log" check box 1235; and a "Do not display and do not save log" check box 1237 with which is associate a log file name input box 1238 and a log file folder radio button 1239 to aid in the selection/entry of the log file name, if the "Do not display and do not save log" check box 1237 is selected.

In FIG. 12, help information may be accessed by selecting (e.g., left clicking on and/or pressing the "H" key) "? Help" radio button 1. In addition, a "Use default values" radio button 2 may be selected to use a predefined set of default task values, a "Next" radio button 3 may be selected to advance to the next screen, and a "Previous" radio button 4 may be selected to go back to the previous screen. Screen 1200 may also include a complexity input window 1250 in which a value for the number of different models used in determining the optimal model may be specified, with 1 model being the lowest complexity and values greater than one being increasingly more complex.

Figure 13:
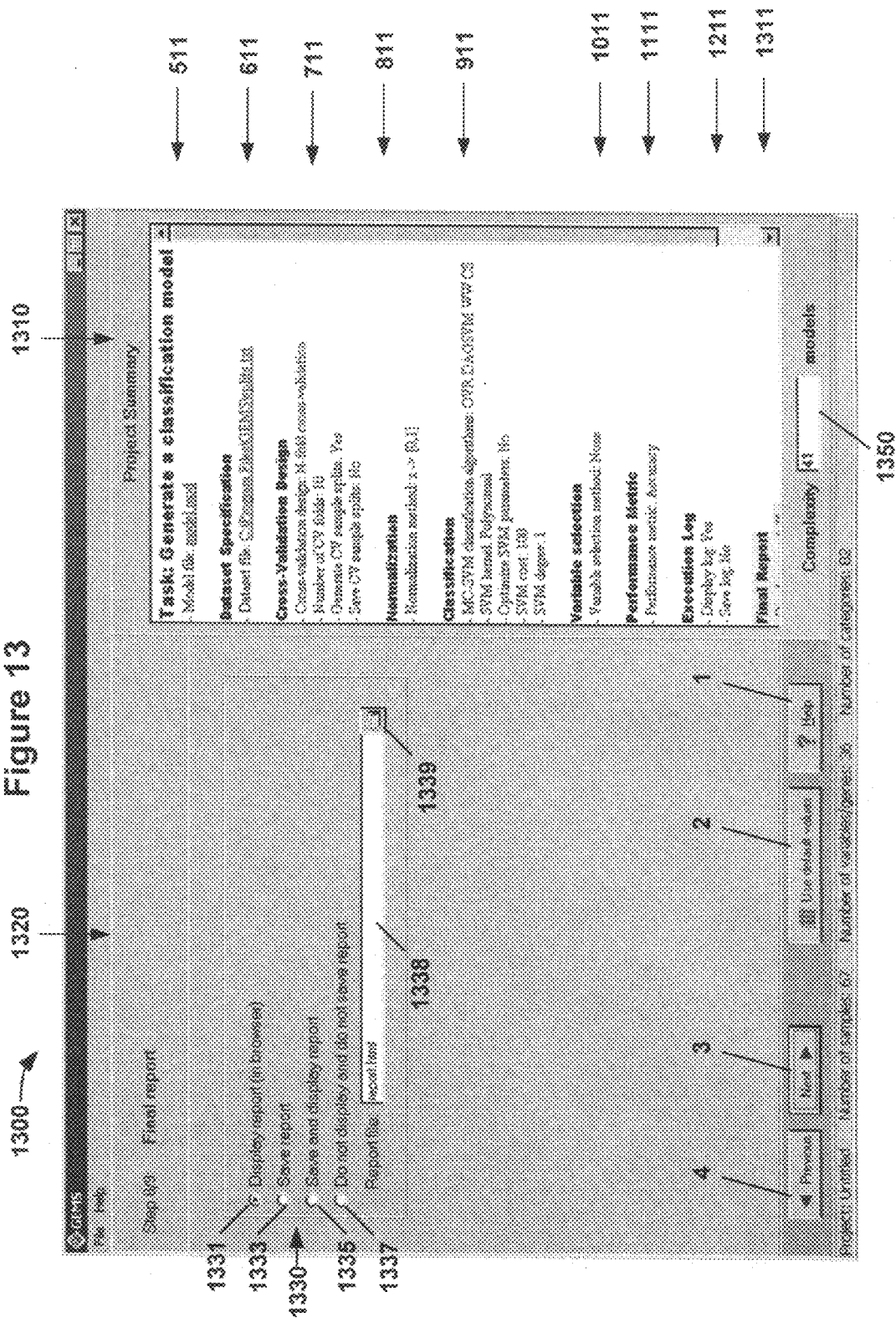
FIG. 13 is a screen shot of a final report selection screen for selecting how the final report will be displayed and/or saved, in accordance with one or more embodiments of the present invention.

FIG. 13 is a screen shot of a final report selection screen for selecting how the final report will be displayed and/or saved, in accordance with one or more embodiments of the present invention. In FIG. 13, an example screen 1300 includes a project summary section 1310 and user interaction section 1320 with a final report option selection subsection 1330. Project summary section 1310 may include the tasks and elements that are available in the model. For example, in project summary section 1310 final report element 1311 is highlighted and displays information on which final report option is to be used to display, print, and/or save the report after execution of the model, as selected in final report option selection subsection 1330. In final report option selection subsection 1330, for example, the check buttons may include a "Display report (in browser)" check box 1331; a "Save report" check box 1333; a "Save and display report" check box 1335; and a "Do not display and do not save report" check box 1337 with which is associated a report file name input box 1338 and a report file folder radio button 1339 to aid in the selection/entry of the report file name, if the "Do not display and do not save report" check box 1337 is selected.

In FIG. 13, help information may be accessed by selecting (e.g., left clicking on and/or pressing the "H" key) "? Help" radio button 1. In addition, a "Use default values" radio button 2 may be selected to use a predefined set of default task values, a "Next" radio button 3 may be selected to advance to the next screen, and a "Previous" radio button 4 may be selected to go back to the previous screen. Screen 1300 may also include a complexity input window 1350 in which a value for the number of different models used in determining the optimal model may be specified, with 1 model being the lowest complexity and values greater than one being increasingly more complex.

Figure 14:
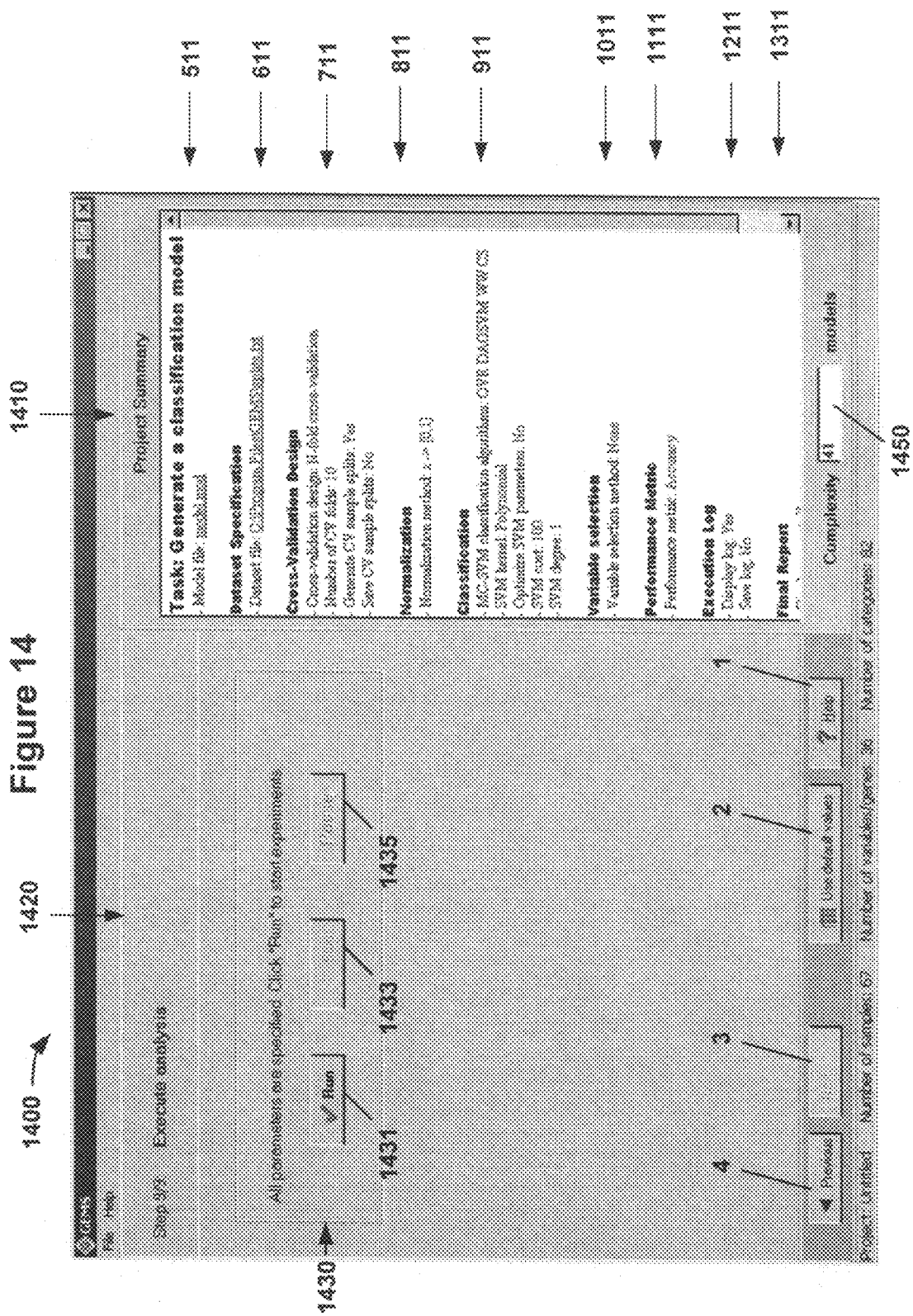
FIG. 14 is a screen shot of an execute analysis screen for starting the analysis, in accordance with one or more embodiments of the present invention.

FIG. 14 is a screen shot of an execute analysis screen for starting the analysis, in accordance with one or more embodiments of the present invention. In FIG. 14, an example screen 1400 includes a project summary section 1410 and user interaction section 1420 with an execute analysis subsection 1430. Project summary section 1410 may include the tasks and elements that are available in the model. For example, project summary section 1410 displays information on all of the selections made by the user up to this point in defining the model. Execute analysis subsection 1430 may include, for example, a "Run" radio button 1431; a "Stop" radio button 1433; and a "Pause" radio button 1435. Both "Stop" radio button 1433 and "Pause" radio button 1435 are grayed-out to indicate that they are currently not active buttons. However, once the user has selected "Run" radio button 1431, "Stop" radio button 1433 and "Pause" radio button 1435 will be made active to control and/or stop the execution of the analysis.

In FIG. 14, help information may be accessed by selecting (e.g., left clicking on and/or pressing the "H" key) "? Help" radio button 1. In addition, a "Use default values" radio button 2 may be selected to use a predefined set of default task values, and a "Previous" radio button 4 may be selected to go back to the previous screen. Although a "Next" radio button 3 is shown, it is not active on this screen, since this is the last screen in the series. Screen 1400 may also include a complexity input window 1450 in which a value for the number of different models used in determining the optimal model may be specified, with 1 model being the lowest complexity and values greater than one being increasingly more complex.

In accordance with one or more embodiments of the present invention, a method for automatically analyzing data and constructing data classification models based on the data may include selecting a best combination of methods from a plurality of classification, predictor selection, and data preparatory methods and determining a best model that corresponds to one or more best parameters of the classification, predictor selection, and data preparatory methods for the data to be analyzed. The method may also include estimating the performance of the best model using new data that was not used in selecting the best combination of methods or in determining the best model; and returning a small set of predictors sufficient for the classification task.

Another embodiment of the present invention may use different cross-validation designs (such as 1-fold cross-validation or leave-one-out-cross-validation). (See, Statnikov A, Tsamardinos I, Dosbayev Y, Aliferis C F. "GEMS: A System for Automated Cancer Diagnosis and Biomarker Discovery from Microarray Gene Expression Data." Int J Med Inform. 2005 August; 74(7-8): 493-501.)

In another embodiment of the present invention, which may be implemented in another computer program, Mass Spectra from MALDI and SELDI Mass Spectrometry may be analyzed instead of micro-array gene expression data. In this embodiment, additional standard data analysis steps specific to mass spectrometry are, generally, added for spectral baseline correction, de-noising, peak detection, and peak alignment before the usual analysis described in the baseline invention. (See, Fananapazir N, Li M, Spentzos D, Aliferis C F. "Formative Evaluation of a Prototype System for Automated Analysis of Mass Spectrometry Data." AMIA Symposium, 2005, which is hereby incorporated by reference herein in its entirety.)

In yet another embodiment of the present invention, error estimation and/or model selection may be accomplished via bootstrapping, repeated N-fold cross-validation, and other prediction error estimation techniques.

In another embodiment of the present invention, various ensembling and model averaging methods may be used to produce an aggregate final data classification model.

In still another embodiment of the present invention, optimization of parameters may be done using theoretical error bounds for a plurality of classifiers (e.g., error bounds from SVM theory).

In a further embodiment of the present invention, a combination of data types may be analyzed (e.g., gene expression, mass spectrometry, imaging, and clinical data).

In yet a further embodiment of the present invention, documents containing text may be classified according to document content. (See, Duda S, Aliferis C F, Miller R A, Statnikov A, Johnson K B. "Extracting Drug-Drug Interaction Articles from MEDLINE to Improve the Content of Drug Databases." AMIA Symposium, 2005.)

In another embodiment of the present invention, peri-operative data, for example, from patients that underwent liver transplantation may be analyzed to derive models for predicting graft failure and to identify a small set of predictive variables.

In yet another embodiment of the present invention, data capturing the diagnoses of physicians upon examination of subjective and objective features may be analyzed to predict and model the behavior of the physician. (See, Sboner A, Aliferis C F. "Modeling Clinical Judgment and Implicit Guideline Compliance in the Diagnosis of Melanomas Using Machine Learning." AMIA Symposium, 2005.)

In still another embodiment of the present invention, the best model found by the method may be explained to the user by learning a decision tree that captures the model's input-output behavior and further reducing the tree to simple decision rules. (See, Sboner A, Aliferis C F. "Modeling Clinical Judgment and Implicit Guideline Compliance in the Diagnosis of Melanomas Using Machine Learning." AMIA Symposium, 2005.)

In a further embodiment of the present invention, the selected predictors may be linked to a plurality of knowledge sources (e.g., gene probes and proteins to regulatory and metabolic pathway databases).

In a still further embodiment of the present invention, sets of default settings corresponding to detailed and quick "canned" analyses may be stored and presented to users who do not wish to specify any parameter ranges or other choices for the data analysis.

A further embodiment of the present invention, a continuous response variable may be predicted by regression techniques.

In a yet further embodiment of the present invention, multiple response variables may be predicted simultaneously.

In a still further embodiment of the present invention, a different sequence of data analysis steps may be used (e.g., normalization can be performed not only before but also after variable selection).

In yet another embodiment of the present invention, model selection and validation may be performed experimentally.

Alternative embodiments of the above-described methods may be implemented in a software program that is stored on a machine-readable medium and that may be executed by a machine, for example, a computer processor. In addition, the software may be implemented to be downloaded to and installed on individual computers over a network, for example, the Internet.

The above description is considered to illustrate the general principles of the invention and is in no way to be construed so as to limit the invention as expressed in the appending claims to the exact construction, implementations and versions shown and described.

APPENDIX A

| Name | Version | Developer | Supervised classification | Cross-validation for performance estimation | Automatic model selection for classifier and gene selection methods | URL |
|---|---|---|---|---|---|---|
| ArrayMiner ClassMarker | 5.2 | Optimal Design, Belgium | K-Nearest Neighbors: Voting | Yes | No | http://www.optimaldesign.com/ArrayMiner |
| Avadis Prophetic | 3.3 | Strand Genomics, U.S.A. | Decision Trees; Neural Networks; Support Vector Machines. | Yes | No | http://avadis.strandgenomics.com/ |
| BRB ArrayTools | 3.2 Beta | National Cancer Institute, U.S.A. | Compound Covariate Predictor; Diagonal Linear Discriminant Analysis; Nearest Centroid; K-Nearest Neighbors; Support Vector Machines. | Yes | No | http://linus.nci.nih.gov/BRB-ArrayTools.html |
| caGEDA | (accessed October 2004) | University of Pittsburgh and University of Pittsburgh Medical Center, U.S.A. | Nearest Neighbors methods; Naïve Bayes Classifier. | Yes | No | http://bioinformatics.upmc.edu/GE2/GEDA.html |
| Cleaver | 1.0 (accessed October 2004) | Stanford University, U.S.A. | Linear Discriminant Analysis | Yes | No | http://classify.stanford.edu |
| GeneCluster2 | 2.1.7 | Broad Institute, Massachusetts Institute of Technology, U.S.A. | Weighted Voting; K-Nearest Neighbors. | Yes | No | http://www.broad.mit.edu/cancer/software |
| GeneLinker Platinum | 4.5 | Predictive Patterns Software, Canada | Neural Networks; Support Vector Machines; Linear Discriminant Analysis; Quadratic Discriminant Analysis; Uniform/Gaussian Discriminant Analysis. | Yes | No | http://www.predictivepatterns.com/ |
| GeneMaths XT | 1.02 | Applied Maths, Belgium | Neural Networks; K-Nearest Neighbors; Support Vector Machines. | Yes | No | http://www.applied-maths.com/genemaths/genemaths.htm |
| GenePattern | 1.2.1 | Broad Institute, Massachusetts Institute of Technology, U.S.A. | Weighted Voting; K-Nearest Neighbors; Support Vector Machines. | Yes | No | http://www.broad.mit.edu/cancer/software |
| Genesis | 1.5.0 | Graz University of Technology, Austria | Support Vector Machines | No | No | http://genome.tugraz.at/Software/Genesis/Genesis.html |
| GeneSpring | 7 | Silicon Genetics, U.S.A. | K-Nearest Neighbors; Support Vector Machines | Yes | No | http://www.silicongenetics.com |
| GEPAS | 1.1 (accessed October 2004) | Natiotial Center for Cancer Research (CNIO), Spain | K-Nearest Neighbors; Support Vector Machines; Diagonal Linear Discriminant Analysis. | Yes | Limited (for number of genes) | http://gepas.bioinfo.cnio.es/tools.html |

APPENDIX A-continued

| Name | Version | Developer | Supervised classification | Cross-validation for performance estimation | Automatic model selection for classifier and gene selection methods | URL |
|---|---|---|---|---|---|---|
| MultiExperiment Viewer | 3.0.3 | The Institute for Genomic Research, U.S.A. | K-Nearest Neighbors: Support Vector Machines. | Yes | No | http://www.tigr.org/software/tm4/mev.html |
| PAM | 1.21a | Stanford University, U.S.A. | Nearest Shrunken Centroids | Yes | Limited (for a single parameter of the classifier) | http://www-stat.stanford.edu/~tibs/PAM/ |
| Partek Predict | 6.0 | Partek, U.S.A. | K-Nearest Neighbors: Nearest Centroid Classifier: Discriminant Analysis. | Yes | Limited (does not allow optimization of the choice of gene selection algorithms) | http://www.partek.com/ |
| Weka Explorer | 3.4.3 | University of Waikato, New Zeland | K-Nearest Neighbors: Decision Trees: Rule Sets: Bayesian Classifiers: Support Vector Machines: Multi-Layer Perceptron: Linear Regression: Logistic Regression: Meta-Learning Techniques (Boosting, Bagging). | Yes | No | http://www.cs.waikato.ac.nz/ml/weka/ |

APPENDIX B

Classification algorithms

K-Nearest Neighbors
Backpropagation Neural Networks
Probabilistic Neural Networks
Multi-Class SVM: One-Versus-Rest
Multi-Class SVM: One-Versus-One
Multi-Class SVM: DAGSVM
Multi-Class SVM by Weston & Watkins
Multi-Class SVM by Crammer & Singer
Weighted Voting: One-Versus-Rest
Weighted Voting: One-Versus-One
Decision Trees: CART
Ensemble classification algorithms
Based on outputs of Multi-Class
SVM methods Majority Voting
Decision Trees: CART
Multi-Class SVM: DAGSVM
Multi-Class SVM: One-Versus-Rest
Multi-Class SVM: One-Versus-One
Based on outputs of all classifiers Majority Voting
Decision Trees: CART

Computational experimental design

Leave-one-out cross-validation for performance
estimation (outer loop) and 10-fold cross-validation
for model selection (inner loop)
10-fold cross-validation for performance estimation
(outer loop) and 9-fold cross-validation for model
selection (inner loop)

Gene selection methods

Signal-to-noise ratio in one-versus-rest fashion
Signal-to-noise ratio in one-versus-one fashion
Kruskal-Wallis nonparametric one-way ANOVA
Ratio of genes between-categories to within-
category sum of squares

Performance metrics

Accuracy
Relative classifier information (entropy-based
performance metric)
Statistical comparison among classifiers Custom randomized permutation procedure

APPENDIX C

| Dataset name | Diagnostic Task | Samples | Number of Variables (genes) | Categories | Reference |
|---|---|---|---|---|---|
| 11_Tumors | 11 various human tumor types | 174 | 12533 | 11 | Su. A. I., Welsh. J. B., Sapinoso. L. M., Kern. S. G., Dimitrov. P., Lapp. H., Schultz. P. G., Powell. S. M., Moskaluk. CA, Frierson. H. F., Jr and Hampton. G. M. (2001) Molecular classification of human carcinomas by use of gene expression signatures. Cancer Res. 61, 7388-7393 |
| 14_Tumors | 14 various human tumor types and 12 normal tissue types | 308 | 15009 | 26 | Ramaswamy. S., Tamayo. P., Rifkin. R., Mukherjee. S., Yeang. C. H., Angelo. M., Ladd. C., Reich. M. Latulippe. E., Mesirov. J. P., et al. (2001) Multiclass cancer diagnosis using tumor gene expression signatures. Proc. Natl Acad. Sci. U.S.A. 98, 15149-15154 |
| 9_Tumors | 9 various human tumor types | 60 | 5726 | 9 | Staunton. J. E., Slonim. D. K., Coller. H. A., Tamayo. P. Angelo. M. J., Park. Scherf. U., Lee. J. K., Reinhold. W. O., Weinstein. J. N., et al. (2001) Chemosensitivity prediction by transcriptional profiling. Proc. Natl Acad. Sci. U.S.A. 98, 10787-10792 |
| Brain_Tumor1 | 5 human brain tumor types | 90 | 5920 | 5 | Pomeroy. S. L., Tamayo. P., Gaasenbeek. M., Sturla. L. M., Angelo. M., McLaughlin. M. E., Kins. J. Y., Goumnerova. L. C., Black. P. M., Lau. C., et al. (2002) Prediction of central nervous system embryonal tumour outcome based on gene expression. Nature. 415, 436-442 |
| Brain_Tumor2 | 4 malignant glioma types | 50 | 10367 | 4 | Nutt. C. L., Mani. D. R., Betensky. R. A., Tamayo. P., Cairncross. J. G., Ladd. C., Pohl. U., Hartmann. C., McLaughlin. M. E., Batchelor. T. T., et al. (2003) Gene expression-based classification of malignant gliomas correlates better with survival than histological classification. Cancer Res., 63, 1602-1607 |
| Leukemia1 | Acute myelogenous leukemia (AML), acute lymphoblastic leukemia (ALL) B-cell, and ALL T-cell | 72 | 5327 | 3 | Golub. T. R., Slonim. D. K., Tamayo. P., Huard. C., Gaasenbeek. M., Mesirov. J. P., Coller. H., Loh. M. L., Downing. J. R., Caligiuri. M. A., Bloomfield. C. D., Lander. E. S. (1999) Molecular classification of cancer: class discovery and class prediction by gene expression monitoring. Science. 286, 531-537 |
| Leukemia2 | AML, ALL, and mixed-lineage leukemia (MLL) | 72 | 11225 | 3 | Armstrong. S. A., Staunton. J. E., Silverman. L. B., Pieters. R., den Boer. M. L., Minden. M. D., Sallan. S. E., Lander. E. S., Golub. T. R., Korsmeyer. S. J. (2002) MLL translocations specify a distinct gene expression profile that distinguishes a unique leukemia. Nat. Genet., 30, 41-47 |
| Lung_Cancer | 4 lung cancer types and normal tissues | 203 | 12600 | 5 | Bhattacherjee. A., Richards. W. G., Staunton. J. L., Li. C., Monti. S., Vasa. P., Ladd. C., Beheshti. J., Bueno. R., Gillette. M., et al. (2001) Classification of human lung carcinomas by mRNA expression profiling reveals distinct adenocarcinoma subclasses. Proc. Natl Acad. Sci. U.S.A. 98, pp. 13790-13795. |
| SRBCT | Small, round blue cell tumors (SRBCT) of childhood | 83 | 2308 | 4 | Khan. J., Wei. J. S., Ringner. M., Saal. L. H., Ladanyi. M., Westermann. F., Berthold. F., Schwab. M., Antonescu. C. R., Peterson. C., Meltzer. P. S., (2001) Classification and diagnostic prediction of cancers using gene expression profiling and artificial neural networks. Nat. Med., 7. pp. 673-679. |
| Prostate_Tumor | Prostate tumor and normal tissues | 102 | 10509 | 2 | Singh. D., Febbo. P. G., Ross. K., Jackson. D. G., Manola. J., Ladd. C., Tamayo. P., Renshaw. A. A., D'Amico. A. V., Richie. J. P., et al. (2002) Gene expression correlates of clinical prostate cancer behavior. Cancer Cell., pp. 203-209. |
| DLBCL | Diffuse large b-cell lymphomas (DLBCL) and follicular lymphomas | 77 | 5469 | 2 | Shipp. M. A., Ross. K. N., Tamayo. P., Weng. A. P., Kutok. J. L., Aguiar. R. C., Gaasenbeek. M., Angelo. M., Reich. M., Pinkus. G. S., et al. (2002) Diffuse large B-cell lymphoma outcome prediction by gene expression profiling and supervised machine learning. Nat. Med., 8, 68-74 |

APPENDIX D

Classification algorithms

Multi-Class SVM: One-Versus-Rest
Multi-Class SVM: One-Versus-One
Multi-Class SVM: DAGSVM
Multi-Class SVM by Weston & Watkins
Multi-Class SVM by Crammer & Singer
Gene selection methods Signal-to-noise ratio in one-versus-rest fashion
Signal-to-noise ratio in one-versus-one fashion
Kruskal-Wallis nonparametric one-way ANOVA
Ratio of genes between-categories to within-category sum of squares
HITON_PC
HITON_MB
Normalization techniques For every gene x → [a, b]
For every gene x → [x − Mean(x)]/Std(x)
For every gene x → x/Std(x)
For every gene x → x/Mean(x)
For every gene x → x/Median(x)
For every gene x → x/‖x‖
For every gene x → x − Mean(x)
For every gene x → x − Median(x)
For every gene x → |x|
For every gene x → x + |x|
For every gene x → Log(x)
Computational experimental design Leave-one-out cross-validation for performance estimation (outer loop) and N-fold cross-validation for model selection (inner loop)
N-fold cross-validation for performance estimation (outer loop) and (N−1)-fold cross-validation for model selection (inner loop)
Leave-one-out cross-validation for model selection
N-fold cross-validation for model selection
Performance metrics Accuracy
Relative classifier information (entropy-based performance metric)
Area under ROC curve (AUC)

What is claimed is:

1. A data analysis system embodied as a plurality of executable instructions stored on a non-transitory machine readable medium that, when executed by a processor in a computer perform a process comprising:
a first subprocess to estimate the performance of a data classification model using a data set being partitioned into N non-overlapping and balanced subsets and a first cross-validation procedure;
a second subprocess to choose an optimal set of parameters for the data classification model using the N non-overlapping and balanced subsets and a second cross-validation procedure; and
a third subprocess to simultaneously perform optimal model selection and estimate performance of the data classification model using the N non-overlapping and balanced subsets and a nested cross-validation procedure; and
a fourth subprocess to apply obtained model to classify new data.

2. The data analysis system of claim 1 wherein the first subprocess comprises:
a multi-category support vector machine-based classification method.

3. The data analysis system of claim 2 wherein the multi-category support vector machine-based classification method comprises one of:
a one-versus-rest multi-category support vector machine-based classification method;
a one-versus-one multi-category support vector machine-based classification method;
a DAGSVM multi-category support vector machine-based classification method;
a Weston and Watkins multi-category support vector machine-based classification method; and
a Crammer and Singer multi-category support vector machine-based classification method.

4. The data analysis system of claim 1 wherein the first subprocess comprises:
repeating the following for each of the N non-overlapping and balanced subsets
partitioning the non-overlapping and balanced subset into a training set of N−1 subsets and a testing set of the remaining one Nth subset so that the testing set is different from all prior partitionings;
training a learning procedure on the training set using a constant parameter value;
testing the learning procedure on the testing set; and
storing a performance value for the learning procedure; and
outputting an average performance value of the learning procedure over each of the N testing sets.

5. The data analysis of claim 4 wherein the second subprocess comprises:
repeating the following for each of a plurality of parameter values
repeating the following for each of the N non-overlapping and balanced subsets
partitioning the non-overlapping and balanced subset into a training set of N−1 subsets and a testing set of the remaining one Nth subset so that the testing set is different from all prior partitionings;
training a learning procedure on the training set using a current parameter value from the plurality of parameter values; and
testing the learning procedure on the testing set; and
storing an average performance value of the learning procedure over each of the N testing sets for a current one of the plurality of parameter values; and
determining a parameter having a best performance value of the average performance values; and
training the learning procedure using the data set and the parameter having the best performance value to output the best data classification model.

6. The data analysis system of claim 1 wherein the third subprocess comprises:
repeating the following for each of the N non-overlapping and balanced subsets
partitioning the N non-overlapping and balanced subsets into a training set of N−1 subsets;
reserving the Nth non-overlapping and balanced subset as a testing set;
repeating the following for each of a plurality of parameter values
repeating the following for each of the N−1 subsets in the training set
partitioning the N−1 training set into an N−2 subset training validation set and a single subset testing validation set;
training a learning procedure on the N−2 training validation set from the training set using a current one of the plurality of parameter values; and
testing the learning procedure on the single subset in the testing validation set;

storing an average performance value of the learning procedure over each of the N−1 testing validation sets for the current one of the plurality of parameter values;

determining a parameter having a best performance value of the average performance values;

training the learning procedure using the data set and the parameter having the best performance value; and testing the learning procedure trained using the data set and the parameter having the best performance value on the testing set; and outputting an average performance value of the learning procedure trained using the data set and the parameter having the best performance value over each of the N testing sets.

7. A non-transitory machine readable medium having stored thereon a plurality of executable instructions that, when executed by a computer processor, perform a method comprising:

estimating the performance of a plurality of data classification models using a data set being partitioned into N non-overlapping and balanced subsets and a first cross-validation procedure;

choosing an optimal set of parameters for each of the plurality of data classification models using the N non-overlapping and balanced subsets and a second cross-validation procedure;

performing optimal model selection and estimating performance of the data classification model using the N non-overlapping and balanced subsets and a nested cross-validation procedure; and applying obtained model to classify new data.

8. The non-transitory machine readable medium of claim 7 wherein the estimating the performance of a plurality of data classification models comprises:

using a multi-category support vector machine-based classification method.

9. The non-transitory machine readable medium of claim 8 wherein the multi- category support vector machine-based classification method comprises one of:

a one-versus-rest multi-category support vector machine-based classification method;

a one-versus-one multi-category support vector machine-based classification method;

a DAGSVM multi-category support vector machine-based classification method;

a Weston and Watkins multi-category support vector machine-based classification method; and a Crammer and Singer multi-category support vector machine-based classification method.

10. The non-transotory machine readable medium of claim 7 wherein the estimating the performance of a plurality of data classification models comprises:

repeating the following for each of the N non-overlapping and balanced subsets partitioning the N non-overlapping and balanced subsets into a training set of N−1 subsets;

reserving the Nth non-overlapping and balanced subset as a testing set;

training a learning procedure on the training set using a constant parameter value; and testing the learning procedure on the testing set; and outputting an average performance value of the learning procedure over each of the N testing sets.

11. The non-transitory machine readable medium of claim 7 wherein the choosing an optimal set of parameters for each of the plurality of data classification models comprises:

repeating the following for each of a plurality of parameter values repeating the following for each of the N non-overlapping and balanced subsets partitioning the N non-overlapping and balanced subsets into a training set of N−1 subsets;

reserving the Nth non-overlapping and balanced subset as a testing set;

training a learning procedure on the training set using a constant parameter value; and testing the learning procedure on the testing set; and storing an average performance value of the learning procedure over each of the N testing sets for a current one of the plurality of parameter values;

determining a parameter having a best performance value of the average performance values; and training the learning procedure using the data set and the parameter having the best performance value to output the best model.

12. The non-transitory machine readable medium of claim 7 wherein the performing optimal model selection and estimating performance of each of the plurality of data classification models comprises:

repeating the following for each of the N non-overlapping and balanced subsets partitioning the N non-overlapping and balanced subsets into a training set of N−1 subsets;

reserving the Nth non-overlapping and balanced subset as a testing set;

repeating the following for each of a plurality of parameter values repeating the following for each of the N−1 subsets in the training set partitioning the N−1 training set into an N−2 subset training validation set and a single subset testing validation set;

training a learning procedure on the N−2 training validation set from the training set using a current one of the plurality of parameter values; and testing the learning procedure on the single subset in the testing validation set;

storing an average performance value of the learning procedure over each of the N−1 testing validation sets for the current one of the plurality of parameter values;

determining a parameter having a best performance value of the average performance values;

training the learning procedure using the data set and the parameter having the best performance value; and testing the learning procedure trained using the data set and the parameter having the best performance value on the testing set; and outputting an average performance value of the learning procedure trained using the data set and the parameter having the best performance value over each of the N testing sets.

13. A non-transitory machine readable medium having stored thereon a plurality of executable instructions that, when executed by a computer processor, perform a method comprising:

selecting a plurality of data classification models using a plurality of nested cross-validation techniques;

estimating the performance of the plurality of data classification models using a data set being partitioned into N non-overlapping and balanced subsets and a first cross-validation procedure;

choosing an optimal set of parameters for each of the plurality of data classification models using the N non-overlapping and balanced subsets and a second cross-validation procedure;

performing optimal model selection and estimating performance of the data classification models using the N non-overlapping and balanced subsets and a nested cross-validation procedure; and applying obtained model to classify new data.

14. The method of claim 13 wherein the selecting the plurality of data classification models comprises:

selecting the plurality of data classification models using an N-fold cross-validation technique or a leave-one-out cross-validation technique.

15. The method of claim 14 wherein the selecting the plurality of data classification models using the N-fold cross-validation technique or the leave-one-out cross-validation technique occurs in a statistically unbiased fashion.

16. A non-transitory machine-readable medium having stored thereon a plurality of machine-executable instructions that, when executed by a computer processor, perform a method comprising:

receiving a plurality of inputs that specify a plurality of parameters for a classification model;

determine a best data classification model from a predetermined plurality of data classification models using the plurality of inputs by estimating the performance of the predetermined plurality of data classification models using a data set being partitioned into N non-overlapping and balanced subsets and a first cross-validation procedure;

choosing an optimal set of parameters for each of the predetermined plurality of data classification models using the N non-overlapping and balanced subsets and a second cross-validation procedure;

performing optimal model selection and estimating performance of the data classification models using the N non-overlapping and balanced subsets and a nested cross-validation procedure; and applying obtained model to classify new data.

17. The non-transitory machine-readable medium of claim 16 wherein the selecting the plurality of data classification models comprises:

selecting the plurality of data classification models using an N-fold cross-validation technique or a leave-one-out cross-validation technique.

18. The non-transitory machine-readable medium of claim 17 wherein the selecting the plurality of data classification models using the N-fold cross-validation technique or the leave-one-out cross-validation technique occurs in a statistically unbiased fashion.

* * * * *

UNITED STATES PATENT AND TRADEMARK OFFICE
CERTIFICATE OF CORRECTION

PATENT NO.         : 7,912,698 B2
APPLICATION NO.    : 11/510847
DATED              : March 22, 2011
INVENTOR(S)        : Statnikov et al.

It is certified that error appears in the above-identified patent and that said Letters Patent is hereby corrected as shown below:

Title Page,
Item (57) Please replace last sentence of Abstract as follows:

"The method also includes estimating the performance of the best model using new data that was not used in selecting the best combination of methods or in determining the best model; and returning a small set of predictors sufficient form the classification task."

Column 30, lines 32-37 – Please correct the format of Claim 12 as follows:

"repeating the following for each of a
   plurality of parameter values;
repeating the following for each of the
   N-1 subsets in the training set;
partitioning the N-1 training set into an
   N-2 subset training validation set and a single subset testing validation set;"

Signed and Sealed this
Sixteenth Day of August, 2011

David J. Kappos
*Director of the United States Patent and Trademark Office*